United States Patent
Gryaznov et al.

(10) Patent No.: US 9,732,114 B2
(45) Date of Patent: *Aug. 15, 2017

(54) COMPOUNDS HAVING ANTI-ADHESIVE EFFECTS ON CANCER CELLS

(71) Applicants: Sergei M. Gryaznov, San Mateo, CA (US); Jerry W. Shay, Dallas, TX (US); Woodring Wright, Arlington, TX (US)

(72) Inventors: Sergei M. Gryaznov, San Mateo, CA (US); Jerry W. Shay, Dallas, TX (US); Woodring Wright, Arlington, TX (US)

(73) Assignees: GERON CORPORATION, Menlo Park, CA (US); BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,443

(22) Filed: Jul. 21, 2014

(65) Prior Publication Data

US 2014/0329890 A1 Nov. 6, 2014

Related U.S. Application Data

(62) Division of application No. 12/524,844, filed as application No. PCT/US2008/001277 on Jan. 30, 2008, now Pat. No. 8,785,409.

(60) Provisional application No. 60/898,515, filed on Jan. 30, 2007.

(51) Int. Cl.
*C07H 21/00* (2006.01)
*A61K 47/48* (2006.01)
*C07H 21/04* (2006.01)

(52) U.S. Cl.
CPC ....... *C07H 21/00* (2013.01); *A61K 47/48046* (2013.01); *C07H 21/04* (2013.01)

(58) Field of Classification Search
None
See application file for complete search history.

(56) References Cited

U.S. PATENT DOCUMENTS

| | | |
|---|---|---|
| 4,757,141 A | 7/1988 | Fung et al. |
| 4,904,582 A | 2/1990 | Tullis |
| 4,958,013 A | 9/1990 | Letsinger |
| 5,411,947 A | 5/1995 | Hostetler et al. |
| 5,416,203 A | 5/1995 | Letsinger |
| 5,420,330 A | 5/1995 | Brush |
| 5,563,050 A | 10/1996 | Peyman et al. |
| 5,756,476 A | 5/1998 | Epstein et al. |
| 5,763,208 A | 6/1998 | Bischofberger et al. |
| 5,837,694 A | 11/1998 | Barrett |
| 5,846,723 A | 12/1998 | Kim et al. |
| 5,856,461 A | 1/1999 | Colote et al. |
| 5,952,490 A | 9/1999 | Hanecak et al. |
| 5,965,720 A | 10/1999 | Gryaznov et al. |
| 6,001,991 A | 12/1999 | Dean et al. |
| 6,015,710 A | 1/2000 | Shay et al. |
| 6,080,727 A | 6/2000 | Zupi |
| 6,153,737 A | 11/2000 | Manoharan et al. |
| 6,166,188 A | 12/2000 | Cook et al. |
| 6,221,850 B1 | 4/2001 | McKay et al. |
| 6,235,886 B1 | 5/2001 | Manoharan et al. |
| 6,265,558 B1 | 7/2001 | Cook et al. |
| 6,350,853 B1 | 2/2002 | Nielsen et al. |
| 6,395,492 B1 | 5/2002 | Manoharan et al. |
| 6,448,392 B1 | 9/2002 | Hostetler et al. |
| 6,608,036 B1 | 8/2003 | Gryaznov et al. |
| 6,762,169 B1 | 7/2004 | Manoharan |
| 7,067,497 B2 | 6/2006 | Hanecak et al. |
| 7,368,436 B2 | 5/2008 | Gleave et al. |
| 7,494,982 B2 | 2/2009 | Gryaznov et al. |
| 2003/0096776 A1 | 5/2003 | Hanecak et al. |
| 2003/0096980 A1 | 5/2003 | Froehler et al. |
| 2003/0138814 A1 | 7/2003 | Gryaznov et al. |
| 2007/0015723 A1 | 1/2007 | Hanecak et al. |
| 2007/0270363 A1 | 11/2007 | Bennett et al. |
| 2007/0275919 A1 | 11/2007 | Gryaznov et al. |

FOREIGN PATENT DOCUMENTS

| | | |
|---|---|---|
| WO | WO 90/10448 | 9/1990 |
| WO | WO 91/14696 | 10/1991 |
| WO | WO 93/10820 | 6/1993 |
| WO | WO 93/12135 | 6/1993 |
| WO | WO 94/08053 | 4/1994 |
| WO | WO 96/01835 | 1/1996 |
| WO | WO 96/39414 | 12/1996 |
| WO | WO 96/39531 | 12/1996 |
| WO | WO 97/14440 | 4/1997 |
| WO | WO 97/37691 | 10/1997 |
| WO | WO 97/38013 | 10/1997 |
| WO | WO 97/48795 | 12/1997 |
| WO | WO 98/03646 | 1/1998 |
| WO | WO 98/05675 | 2/1998 |
| WO | WO 98/33806 | 8/1998 |
| WO | WO 98/49183 | 11/1998 |
| WO | WO 98/51278 | 11/1998 |
| WO | WO 99/54459 | 10/1999 |
| WO | WO 01/18015 | 3/2001 |
| WO | WO 02/34879 | 5/2002 |
| WO | WO 2004/029277 | 4/2004 |
| WO | WO 2005/023994 | 3/2005 |

OTHER PUBLICATIONS

Jackson, et al. (2007) "Antiadhesive Effects of GRN163L—An Olgionucleotide N3'→p5' Thio-Phosphoramidate Targeting Telomerase", Cancer Research, 67(3): 1121-29.*

(Continued)

*Primary Examiner* — Robert M Kelly
(74) *Attorney, Agent, or Firm* — King & Spalding LLP

(57) ABSTRACT

Compounds of the form O-(x-L)n, where O is an oligonucleoside having at least a plurality of N3'→P5' thiophosphoramidate (NPS) internucleoside linkages, a conjugated lipid moiety L, and at least one G-rich sequence motif as described, are effective to morphologically alter and reduce adhesion of cancer cells.

15 Claims, 23 Drawing Sheets

(56) References Cited

OTHER PUBLICATIONS

Asai et al., "A Novel Telomerase Template Antagonist (GRN163) as a Potential Anticancer Agent", Cancer Res., vol. 63, pp. 3931-3939 (2003).
Chirila et al., "The use of synthetic polymers for delivery of therapeutic antisense oligodeoxynucleotides", Biomaterials vol. 23, pp. 321-342 (2002).
Crooke et al., "Pharmacokinetic properties of several novel oligonucleotide analogs in mice", J. Pharmacol. Exp. Ther., vol. 277, No. 2, pp. 923-937 (1996).
Dikmen, Z.G., G.C. Gellert, S. . Jackson, S. Giyaznov, R. Tressler. P. Dogan, W.E. Wright and J.W. Shay. 2005. In vivo Inhibition of Lung Cancer by GRN163L: A Novel Human Telomerase Inhibitor. Cancer Res. 65:7866-7873.
Fiedler et al., "Growth inhibition of pancreatic tumor cells by modified antisense oligodeoxynucleotides", Langenbeck's Arch. Surg., vol. 383, No. 3-4, pp. 269-275 (1998).
Fleser, A. Dissertation from the Univ. Montreal, (1997),pp. 1-165.
Gellert, G., Z. Dikmen, W. Wright, S. Gryaznov, and J. Shay. 2005a. Effects of a novel telomerase inhibitor, GRN163L, in human breast cancer. Br Cancer Res Treat: 1-9.
Gellert, G., S. Jackson, Z. Dikmen, W. Wright, and J. Shay 2005b, Telomerase as therapeutic target in cancer. Drug Discovery Today: Disease Mechanisrns 2:159-64.
Gerster et al., "Quantitative analysis of modified antisense oligonucleotides in biological fluids using cationic nanoparticles for solid-phase extraction", Anal. Biochem., vol. 262, No. 2, pp. 177-184 (1998).
Gryaznov et al., "Modulation of oligonucleotide duplex and triplex stability via hydrophobic interactions", Nucl. Acids Res., vol. 21, pp. 5909-5915 (1993).
Gryaznov, S. et al., "Oligonucleotide N3'→P5' phosphoramidates as antisense agents", Nucl. Acids Res. 24(8), (1996),pp. 1508-1514.
Herbert et al., "Inhibition of human telomerase in immortal human cells leads to progressive telomere shortening and cell death", Proc. Natl. Acad. Sci. USA, vol. 96, No. 25, pp. 14276-14281 (1999).
Herbert, et al. (2002) "Oligonucleotide N3'—+P5' phorsphoramidates as efficient telomerase inhibitors", Oncogene, 21 (4): 638-42, p. 641.
International Search Report and Written Opinion for PCT application PCT/US2008/001277, Sep. 16, 2008, 8 page s (2008). To Gryaznov, Sergei.
Jackson, et al. (2007) "Antiadhesive Effects of GRN163L—An Olgionucleotide N3'—+p5' Thio-Phosphoramidate Targeting Telomerase", Cancer Research, 67(3): 1121-29.
Jen et al., "Suppression of gene expression by targeted disruption of messenger RNA: available options and current strategies", Stem Cells, vol. 18, pp. 307-319 (2000).
Khaled, Z., L. Benimetskaya, R. Zeltser, T. Khan, H. Sharma, R. Narayanan, and C. Stein 1996. Multiple mechanisms may contribute to the cellular anti-adhesive effects of phosphorothioate oligodeoxynucleotides. Nucl. Acids Res. 24:737-745.
Leonetti, C. et al., "Encapsulation of c-myc antisense oligodeoxynucleotides in lipid particles improves antitumoral efficacy in vivo in a human melanoma line", Cancer Gene Ther. 8(6), (2001),pp. 459-468.

MacKellar et al., "Synthesis and physical properties of anti-HIV antisense oligonucleotides bearing terminal lipophilic groups", Nucl. Acids Res., vol. 20, No. 13, pp. 3411-3417 (1992).
Manoharan, "Oligonucleotide conjugates as potential antisense drugs with improved uptake, biodistribution, targeted delivery, and mechanism of action", Antisense & Nucl. Acid Drug Dev., vol. 12, pp. 103-128 (2002).
Manoharan et al., "Cholic acid-oligonucleotide conjugates for antisense applications", Bioorg. Med. Chem. Lett., vol. 4, No. 8, pp. 1053-1060 (1994).
Mishra et al., "Improved leishmanicidal effect of phosphorotioate antisense oligonucleotides by LDL-mediated delivery", Biochim. Biophys. Acta, vol. 1264, No. 2, pp. 229-237 (1995).
Nelson et al., "Oligonucleotide labeling methods. 3. Direct labeling of oligonucleotides employing a novel, non-nucleosidic, 2-aminobuty1-1,3-propanediol backbone", Nucl. Acids Res., vol. 20, No. 23, pp. 6253-6259 (1992).
Pruzan et al., "Allosteric inhibitors of telomerase: oligonucleotide N3'→P5' phosporamidates", Nucl. Acids Res., vol. 30, No. 2, pp. 559-568 (2002).
Saison-Behmoaras et al., "Short modified antisense oligonucleotides directed against Ha-ras point mutation induce selective cleavage of the mRNA and inhibit T24 cells proliferation", EMBO J., vol. 10, No. 5, pp. 1111-1118 (1995).
Schirmeister-Tichy et al., "Synthesis, Characterization, and Biological Activities of New Potential Antiviral agents: (2'-5')Adenylate trimer analogs containing 3'-deoxy-3'-(hexadecanoylamino)adenosine at the 2'-terminus", Helvetica Chimica Acta, vol. 82, pp. 597-613 (1999).
Shea et al., "Synthesis, hybridization properties and antiviral activity of lipid-oligodeoxynucleotide conjugates", Nucl. Acids Res., vol. 18, No. 13, pp. 3777-3783 (1990).
Shea-Herbert et al., "Oligonucleotide N3'→P5' phosphoramidates as efficient telomerase inhibitors", Oncogene, vol. 21, pp. 638-642 (2002).
Skorski, T. et al., "Antileukemia effect of c-myc N3'→P5' phosphoramidate antisense oligonucleotides in vivo", Proc. Natl. Acad. Sci. USA 94, (1997),pp. 3966-3971.
Smith, J. et al., "Antisense c-myc and immunostimulatory oligonucleotide inhibition of tumorgenesis in a murine B-cell lymphoma transplant model", *J. Natl. Cancer Inst. 90(15)*, (1998),pp. 1146-1154.
Stein, "Is irrelevant cleavage the price of antisense efficacy?", Pharmacol. Ther., vol. 85, pp. 231-236 (2000).
Will et al., "Attachment of Vitamin E Derivatives to Oligonucleotides during Solid-Phase Synthesis", Tetrahedron Lett., vol. 33, No. 19, pp. 2729-2732 (1992).
Fleser et al., "Conjugation of c-myc antisense DNA with Cholesterol Significantly Increases In Vivo Oligomer Vascular Retention" Circulation 92(8) Suppl. I, Abstract No. 1407, (1995)).
Herbert, B.S. et al., "Lipid modification of GRN163, an N3'-P5' thio-phosphoramidate oligonucleotide, enhances the potency of telomerase inhibition" Oncogene 24(33) 5262-5268 (2005).
Herbert et al., "Inhibition of human telomerase in immortal human cells leads to progressive telomere shortening and cell death" PNAS USA vol. 96, No. 25, 14276-14281 (1999).

\* cited by examiner

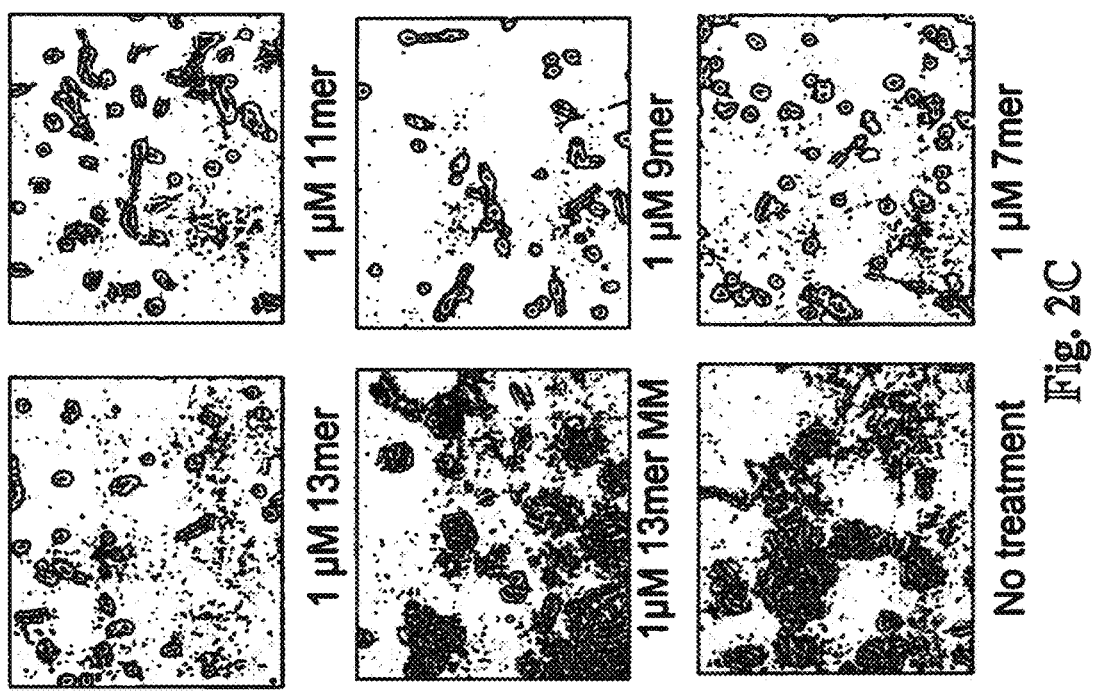

A. Control

B. Mismatch

C. GRN163L

D. 163L 5MeCyt

G. 163L-ribo

F. 163L 2'-OH rA

SEQUENCE LISTING

<160> NUMBER OF SEQ ID NOS: 8

<210> SEQ ID NO 1
<211> LENGTH: 451
<212> TYPE: RNA
<213> ORGANISM: Homo sapiens

<400> SEQUENCE: 1 gguugcgga gguggggccu gggagggug guggccauuu uuugucuaac ccuaacugag    60
aagggcguag gcgccgugcu uuugcuccc gcgcgcuguu uuucucgcug acuuucagcg   120
ggcggaaaag ccucggccug ccgccuucca ccguucauuc uagagcaaac aaaaaaugu   180 agcugcuggc ccguucgccc cucccgggga ccugcggcg gucgccugcc cagccccga    240 accccgccug gaggccgcgg ucggcccggg gcuucuccgg aggcacccac ugccaccgcg   300
aagaguuggg cucugucagc cgcgggucuc ucgggggcga gggcgagguu cagggccuuuc   360 aggccgcagg aagaggaacg gagcgaguc ccgcgcgcgg cgcgauuccc ugagcugugg    420
gacgugcacc caggacucgg cucacacaug c                                  451

<210> SEQ ID NO 2
<211> LENGTH: 13
<212> TYPE: DNA
<213> ORGANISM: Artificial Sequence
<220> FEATURE:
<223> OTHER INFORMATION: Synthetic oligomer

<400> SEQUENCE: 2
tagggttaga caa                                                       13

<210> SEQ ID NO 3
<211> LENGTH: 13
<212> TYPE: DNA
<213> ORGANISM: Artificial Sequence
<220> FEATURE:
<223> OTHER INFORMATION: Synthetic oligomer

<400> SEQUENCE: 3
taggtgtaag caa                                                       13

<210> SEQ ID NO 4
<211> LENGTH: 16
<212> TYPE: DNA
<213> ORGANISM: Artificial Sequence
<220> FEATURE:
<223> OTHER INFORMATION: Synthetic oligomer

<400> SEQUENCE: 4
cgtaccacgc tcgcta                                                    16

```
<210> SEQ ID NO 5
<211> LENGTH: 16
<212> TYPE: DNA
<213> ORGANISM: Artificial Sequence
<220> FEATURE:
<223> OTHER INFORMATION: Synthetic oligomer

<400> SEQUENCE: 5
ctagactcgg accctc                                                    16

<210> SEQ ID NO 6
<211> LENGTH: 15
<212> TYPE: DNA
<213> ORGANISM: Artificial Sequence
<220> FEATURE:
<223> OTHER INFORMATION: Synthetic oligomer

<400> SEQUENCE: 6
aacgttgagg ggcat                                                     15

<210> SEQ ID NO 7
<211> LENGTH: 15
<212> TYPE: DNA
<213> ORGANISM: Artificial Sequence
<220> FEATURE:
<223> OTHER INFORMATION: Synthetic oligomer

<400> SEQUENCE: 7
aacgagttgg ggcat                                                     15

<210> SEQ ID NO 8
<211> LENGTH: 15
<212> TYPE: DNA
<213> ORGANISM: Artificial Sequence
<220> FEATURE:
<223> OTHER INFORMATION: Synthetic oligomer

<400> SEQUENCE: 8
gtggaaggcg gcagg                                                     15
```

COMPOUNDS HAVING ANTI-ADHESIVE EFFECTS ON CANCER CELLS

CROSS-REFERENCE TO RELATED APPLICATIONS

This application is a divisional of and claims priority under 35 U.S.C. §120 to commonly owned U.S. non-provisional patent application Ser. No. 12/524,844, which was filed Nov. 17, 2009, is entitled "Compounds Having Anti-Adhesive Effects on Cancer Cells", and issued as U.S. Pat. No. 8,785,409 on Jul. 22, 2014, which itself is a national stage entry of international patent application number PCT/US2008/001277, which was filed on Jan. 30, 2008 and entitled "Compounds Having Anti-Adhesive Effects on Cancer Cells", which itself claims priority to U.S. provisional patent application No. 60/898,515, which was filed on Jan. 30, 2007 and is entitled, "Compounds Having Anti Adhesive Effects on Cancer Cells". This application is also related to U.S. non-provisional patent application Ser. No. 13/830,595 which was filed Mar. 14, 2013 and is entitled "Compounds Having Anti-Adhesive Effects on Cancer Cells". The entire contents of each of the above identified related applications are hereby incorporated herein by reference.

FIELD OF THE INVENTION

The present invention relates to a class of compounds having anti-adhesive activity and related anticancer activity, and their use in anticancer therapy. In particular, the compounds comprise an oligonucleoside component, having a plurality of N3'→P5' thiophosphoramidate (NPS) internucleoside linkages and a sequence containing at least three consecutive guanine (G) nucleobases or at least two closely spaced G dimers, and a lipid moiety conjugated to the oligonucleoside component.

REFERENCES

Aisner, D., W. Wright, and J. Shay. 2002. Telomerase regulation: Not just flipping the switch. *Cur Opin Gen Dev.* 13:80-85.

Akiyama, M., T. Hideshima, M. A. Shammas, T. Hayashi, M. Hamasaki, Y.-T. Tai, P. Richardson, S. Gryaznov, N. C. Munshi, and K. C. Anderson. 2003. Effects of Oligonucleotide N3'→P5' Thio-phosphoramidate (GRN163) Targeting Telomerase RNA in Human Multiple Myeloma Cells. *Cancer Res.* 63:6187-6194.

Asai, A., Y. Oshima, Y. Yamamoto, T.-a. Uochi, H. Kusaka, S. Akinaga, Y. Yamashita, K. Pongracz, R. Pruzan, E. Wunder, M. Piatyszek, S. Li, A. C. Chin, C. B. Harley, and S. Gryaznov. 2003. A Novel Telomerase Template Antagonist (GRN163) as a Potential Anticancer Agent. *Cancer Res.* 63:3931-3939.

Bryan, T., L. Marusic, S. Bacchetti, M. Namba, and R. Reddel. 1997. The telomere lengthening mechanism in telomerase-negative immortal human cells does not involve the telomerase RNA subunit. *Hum. Mol. Genet.* 6:921-926.

Buhr, J., M. Hurtgen, C. Kelm, and K. Schwemmle. 1995. Tumor dissemination after thoracoscopic resection for lung cancer. *J Thorac Cardiovasc Surg.* 110:855-6.

Chai, W., L. P. Ford, L. Lenertz, W. E. Wright, and J. W. Shay. 2002. Human Ku70/80 Associates Physically with Telomerase through Interaction with hTERT. *J. Biol. Chem.* 277:47242-47247.

Chen, Z., K. S. Koeneman, and D. R. Corey. 2003. Consequences of Telomerase Inhibition and Combination Treatments for the Proliferation of Cancer Cells. *Cancer Res.* 63:5917-5925.

Dias, N., and C. Stein. 2002. Potential roles of antisense oligonucleotides in cancer therapy. The example of Bcl-2 antisense oligonucleotides. *Eur J Pharm Biopharm.* 54:263-9.

Dikmen, Z. G., G. C. Gellert, S. Jackson, S. Gryaznov, R. Tressler, P. Dogan, W. E. Wright, and J. W. Shay. 2005. In vivo Inhibition of Lung Cancer by GRN163L: A Novel Human Telomerase Inhibitor. *Cancer Res.* 65:7866-7873.

Djojosubroto, M., A. Chin, N. Go, S. Schaetzlein, M. Manns, S. Gryaznov, C. Harley, and K. Rudolph. 2005. Telomerase antagonists GRN163 and GRN163L inhibit tumor growth and increase chemosensitivity of human hepatoma. *Hematology* 42:1127-1136.

Downey, R., P. McCormack, and J. L. 3rd. 1996. Dissemination of malignant tumors after video-assisted thoracic surgery: a report of twenty-one cases. The Video-Assisted Thoracic Surgery Study Group. *J Thorac Cardiovasc Surg.* 111:954-60.

Feng, J., W. Funk, S. Wang, S. Weinrich, A. Avilion, C. Chiu, R. Adams, E. Chang, R. Allsopp, and J. Yu. 1995. The RNA component of human telomerase. *Science* 269:1236-41.

Forsyth, N., W. Wright, and J. Shay. 2002. Telomerase and differentiation in multicellular organisms: Turn it off, turn it on, and turn it off again. *Differentiation* 69:188-197.

Gellert, G., Z. Dikmen, W. Wright, S. Gryaznov, and J. Shay. 2005a. Effects of a novel telomerase inhibitor, GRN163L, in human breast cancer. *Br Cancer Res Treat:* 1-9.

Gellert, G., S. Jackson, Z. Dikmen, W. Wright, and J. Shay. 2005b. Telomerase as a therapeutic target in cancer. *Drug Discovery Today: Disease Mechanisms* 2:159-64.

Greider, C., and E. Blackburn. 1985. Identification of a specific telomere terminal transferase activity in Tetrahymena extracts. *Cell* 43:405-13.

Gryaznov, S., K. Pongracz, T. Matray, R. Schultz, R. Pruzan, J. Aimi, A. Chin, C. Harley, B.-S. Herbert, J. Shay, Y. Oshima, A. Asai, and Y. Yamashita. 2001. Telomerase inhibitors—oligonucleotide phosphoramidates as potential therapeutic agents. *Nucleosides, Nucleotides and Nucleic Acids* 20:401-10.

Guvakova, M. A., L. A. Yakubov, I. Vlodaysky, J. L. Tonkinson, and C. A. Stein. 1995. Phosphorothioate Oligodeoxynucleotides Bind to Basic Fibroblast Growth Factor, Inhibit Its Binding to Cell Surface Receptors, and Remove It from Low Affinity Binding Sites on Extracellular Matrix. *J. Biol. Chem.* 270:2620-2627.

Herbert, B.-S., G. C. Gellert, A. Hochreiter, K. Pongracz, W. E. Wright, D. Zielinska, A. C. Chin, C. B. Harley, J. W. Shay, and S. M. Gryaznov. 2005. Lipid modification of GRN163, an N3'→P5' thio-phosphoramidate oligonucleotide, enhances the potency of telomerase inhibition. *Oncogene* 24:5262-5268.

Herbert, B.-S., K. Pongracz, J. Shay, and S. Gryaznov. 2002. Oligonucleotide N3'→P5' phosphoramidates as efficient telomerase inhibitors. *Oncogene* 21:638-42.

Keith, W., A. Bilsland, M. Hardie, and T. J. Evans. 2004. Drug Insight: cancer cell immortality-telomerase as a target for novel cancer gene therapies. *Nature Clinical Practice: Oncology* 1:1-9.

Khaled, Z., L. Benimetskaya, R. Zeltser, T. Khan, H. Sharma, R. Narayanan, and C. Stein. 1996. Multiple mechanisms may contribute to the cellular anti-adhesive effects of phosphorothioate oligodeoxynucleotides. *Nucl. Acids Res.* 24:737-745.

Lingner, J., J. Cooper, and T. Cech. 1995. Telomerase and DNA end replication: no longer a lagging strand problem? *Science* 269:1533-4.

Ozawa, T., S. Gryaznov, L. Hu, K. Pongracz, R. Santos, A. Bolle, K. Lamborn, and D. Deen. 2004. Antitumor effects of specific telomerase inhibitor GRN163 in human glioblastoma xenografts. *Neuro-oncol.* 6:218-26.

Perry, P., J. Arnold, and T. Jenkins 2001. Telomerase inhibitors for the treatment of cancer: the current perspective. *Expert Opin Investig Drugs* 10:2141-56.

Resler, E., D. Bearss, and L. Hurley. 2003. Telomere inhibition and telomere disruption as processes for drug targeting. *Annu Rev Pharmacol Toxicol.* 43:359-79.

Sawabata, N., M. Ohta, and H. Maeda. 2000. Fine-Needle Aspiration Cytologic Technique for Lung Cancer Has a High Potential of Malignant Cell Spread Through the Tract. *Chest* 118:936-939.

Shay, J., and S. Bacchetti. 1997. A survey of telomerase activity in human cancer. *Eur J Cancer* 33:787-91.

Shay, J., and W. Wright. 2004. Senescence and immortalization: role of telomeres and telomerase. *Carcinogenesis* 26:867-74.

Stein, C., and Y. Cheng. 1993. Antisense oligonucleotides as therapeutic agents—is the bullet really magical? *Science* 261:1004-12.

Wang, E. S., K. Wu, A. C. Chin, S. Chen-Kiang, K. Pongracz, S. Gryaznov, and M. A. S. Moore. 2004. Telomerase inhibition with an oligonucleotide telomerase template antagonist: in vitro and in vivo studies in multiple myeloma and lymphoma. *Blood* 103:258-266.

White, L., W. Wright, and J. Shay. 2001. Telomerase inhibitors. *Trends Biotechnol.* 19:114-20.

Yi, X., V. M. Tesmer, I. Savre-Train, J. W. Shay, and W. E. Wright. 1999. Both Transcriptional and Posttranscriptional Mechanisms Regulate Human Telomerase Template RNA Levels. *Mol. Cell. Biol.* 19:3989-3997.

BACKGROUND OF THE INVENTION

A major challenge in the development of novel anti-cancer strategies is the elucidation of molecular targets which are preferentially regulated in human tumors. Greater than 90% of all human cancer cells display robust activation of telomerase (Shay and Bacchetti, 1997), a unique reverse transcriptase consisting of two major components, the RNA moiety (hTR or hTERC) and the catalytic subunit (hTERT) (Feng et al., 1995; Greider and Blackburn, 1985; Lingner et al., 1995). In contrast, normal human cells are devoid of telomerase activity, with the exception of male germline cells and the proliferative cells of renewal tissues (Aisner et al., 2002; Forsyth et al., 2002; Shay and Wright, 2004). Telomerase activation is necessary for most cancer cells to replicate indefinitely and thereby enable tumor growth and subsequent metastasis.

In the last decade, a variety of methods have been devised to inhibit telomerase for cancer therapy (Gellert et al., 2005b; Resler et al., 2003; White et al., 2001). Oligonucleotide-based telomerase inhibitors that target the hTR component of telomerase have been described (Gryaznov et al., 2001). Preferred oligonucleotide-based telomerase inhibitors are N3'→P5' thiophosphoramidate-linked (NPS) oligonucleotides, which have been shown to have a high thermodynamic duplex stability, as well as intracellular hydrolytic stability (Herbert et al., 2002).

The prototype NPS oligonucleotide telomerase inhibitor, having SEQ ID NO: 2 (TAG GGT TAG ACA A) and designated GRN163, causes reversible telomerase inhibition and subsequent telomere shortening in human mammary epithelial cells (Herbert et al., 2002). GRN163-induced telomere erosion also correlates with the induction of senescence or apoptosis in prostate cancer, multiple myeloma and non-Hodgkins lymphoma cells and a reduction of tumor growth in myeloma and glioblastoma xenograft models (Asai et al., 2003; Ozawa et al., 2004; Wang et al., 2004).

A second generation oligonucleotide-based telomerase inhibitor, designated GRN163L, includes a palmitoyl (C16) moiety conjugated to the 5'-terminus of GRN163 (Herbert et al., 2005). This lipid modification increases intracellular uptake, inhibition of telomerase, rate of telomere shortening, and growth inhibition and apoptosis in human mammary epithelial cell and hepatoma cell lines, relative to the unconjugated oligonucleotide (Djojosubroto et al., 2005; Herbert et al., 2005). GRN163L exhibits a multitude of anti-tumorigenic end points in lung and breast cancer cells (Dikmen et al., 2005; Gellert et al., 2005a). In vivo, the compound diminishes the tumor burden of metastatic human lung cancer and orthotopic human breast cancer cells in xenograft mouse models (Dikmen et al., 2005; Gellert et al., 2005a). The activity of GRN163L as an anti-cancer agent has been correlated with its observed ability to inhibit telomerase activity, in a dose- and sequence-dependent manner, via direct interaction with hTR.

SUMMARY OF THE INVENTION

The present invention includes, in one aspect, a compound having a structure represented by O-(x-L)n. In this structure, (a) O is a polynucleoside moiety comprising a sequence of nucleosides joined by internucleoside linkages, wherein (i) at least 50% of said linkages are selected from 3'-NH—P(O)(S$^-$)-5' (i.e., N3'→P5' thiophosphoramidate linkages) and 3'-NH—P(O)(S—)—O—R—Y—P(O)(S$^-$)-5', where Y is O or, preferably, NH, and R is a stable linear chain two to six atoms in length having bonds selected from alkyl, alkenyl, ether, thioether, and amino; and (ii) said sequence includes at least one G-rich motif selected from GGG and GG(W)$_{1-3}$GG, where G is guanosine and W is a nucleoside or the moiety —O—R—, where R is as defined above, and the linkages within this motif are N3'→P5' thiophosphoramidate (3'-NH—P(O)(S—)-5') linkages or phosphorothioate (3'-O—P(O)(S—)-5') linkages, and are preferably N3'→P5' thiophosphoramidate linkages;

(b) x is an optional linker group, (c) L is a lipid moiety, and (d) n is 1 or 2, and is preferably 1;

with the proviso that, when said oligonucleoside O includes a sequence seven or more nucleobases in length that is complementary to a region of hTR (SEQ ID NO: 1), the compound O-(x-L)n is not a telomerase inhibitor.

In a related aspect, the invention includes a compound having a structure represented by O-(x-L)n, where (a) O is a polynucleoside moiety comprising a sequence of nucleosides joined by internucleoside linkages, wherein (i) at least 50% of said linkages are selected from 3'-NH—P(O)(S$^-$)-5' (i.e., N3'→P5' thiophosphoramidate linkages) and 3'-NH—P(O)(S—)—{OR}$_m$—Y—P(O)(S$^-$)-5'; where Y is O or, preferably, NH; R is a stable linear chain two to six atoms in length having bonds selected from alkyl, alkenyl, ether, thioether, and amino; and m is 1-3, preferably 1; and (ii) said sequence includes at least one G-rich motif selected from GGG and GG(W)$_{1-3}$GG, containing residues G and/or W, where G is guanosine and W is a nucleoside or the moiety —O—R—, where R is as defined above, and the inter-residue linkages within this motif are N3'→P5' thiophosphoramidate (3'-NH—P(O)(S—)-5') linkages or phosphorothioate (3'-O—P(O)(S—)-5') linkages, and are preferably N3'→P5' thiophosphoramidate linkages;

(b) x is an optional linker group,
(c) L is a lipid moiety, and
(d) n is 1 or 2, and is preferably 1;

with the proviso that, when said oligonucleoside O includes a sequence seven or more nucleobases in length that is complementary to a region of hTR (SEQ ID NO: 1), the compound O-(x-L)n is not a telomerase inhibitor.

In a further aspect, the invention includes a compound having a structure represented by O-(x-L)n, where (a) O is a polynucleoside moiety comprising a sequence of nucleosides and linkage moieties, wherein
(i) at least 50% of said linkage moieties are selected from: 3'-NH—P(O)(S$^-$)-5' (i.e., N3'→P5' thiophosphoramidate linkages); 3'-NH—P(O)(S—)—{OR}$_m$—Y—P(O)(S$^-$)-5'; and 3'-Y—R—O—P(O)(S—)-5'; where Y is O or, preferably, NH; R is a stable linear chain two to six atoms in length having bonds selected from alkyl, alkenyl, ether, thioether, and amino; and m is 1-3, preferably 1; and
(ii) said polynucleoside moiety includes at least one G-rich motif selected from GGG and GG(W)$_{1-3}$GG, containing residues G and/or W, where G is guanosine and W is a nucleoside or the moiety —OR—, where R is as defined above, and the inter-residue linkages within this motif are N3'→P5' thiophosphoramidate (3'-NH—P(O)(S—)-5') linkages or phosphorothioate (3'-O—P(O)(S—)-5') linkages, and are preferably N3'→P5' thiophosphoramidate linkages;

(b) x is an optional linker group,
(c) L is a lipid moiety, and
(d) n is 1 or 2, and is preferably 1;

with the proviso that, when said polynucleoside moiety O includes a sequence seven or more nucleobases in length that is complementary to a region of hTR (SEQ ID NO: 1), the compound O-(x-L)n is not a telomerase inhibitor.

The linkage moieties defined in (i) above are typically internucleoside linkages (that is, linking nucleosides together). Linkage moieties of the type Y—R—O—P(O)(S—) may also be linked directly to each other.

Preferably, the compounds of the invention are characterized in that they are not telomerase inhibitors as defined herein.

In selected embodiments, at least 75%, at least 85%, at least 95%, or all, of the internucleoside linkages in O, above, are selected from 3'-NH—P(O)(S$^-$)-5' (NPS) and 3'-NH—P(O)(S—)—{OR}$_m$—Y—P(O)(S$^-$)-5', where m is 1. Preferably, at least 50% of the internucleoside linkages in O are NPS linkages.

Other internucleoside linkages in O; that is, any internucleoside linkages not selected from 3'-NH—P(O)(S$^-$)-5' and 3'-NH—P(O)(S—)—{OR}$_m$—Y—P(O)(S$^-$)-5', are typically other phosphorus-based linkages in which phosphorus links the 5'-oxygen (or, less commonly, 5'-NH) of a nucleoside to a 3'-nitrogen or oxygen atom on an adjacent nucleoside. These include, for example, methylphosphonate, P3'→P5' phosphoramidate, N3'→P5' phosphoramidate (NP), and phosphorothioate (PS) linkages. Of these, most preferred are 3'-NH—P(O)(O$^-$)-5' (NP) linkages.

The variable R above is preferably a linear chain three to five atoms in length having bonds selected from alkyl and ether linkages. In one embodiment, R is —(CH$_2$)$_n$—, where n is 3 to 5, preferably 3.

The sum of nucleosides and groups —OR— in the polynucleoside moiety (oligonucleoside) O is preferably from 5 to about 30, more preferably from 5 to about 20, or from 7 to about 15. The ratio of nucleosides to groups —OR— in the oligonucleoside O is preferably 1:1 or greater.

In one embodiment, the G-rich sequence motif comprises at least three consecutive guanosine (G) nucleosides directly linked by NPS linkages. In another embodiment, the G-rich sequence motif GG(W)$_{1-3}$GG, where G is guanosine and W is a nucleoside, and the inter-residue linkages within the motif are N3'→P5' thiophosphoramidate (NPS) linkages.

The lipid L preferably comprises a linear hydrocarbon moiety at least 12 carbon atoms in length, and is attached to the 3' or 5' terminus of the oligonucleoside O. In selected embodiments, the lipid L is a C12 to C24 linear hydrocarbon, preferably a saturated or monounsaturated hydrocarbon. For example, L can be a palmitic or oleic acid derivative, attached to a terminus of O via e.g. a glycerol or aminoglycerol linker as described herein.

Selected compounds of the invention contain at least one linkage of the type 3'-NH—P(O)(S—)—O—R—Y—P(O)(S$^-$)-5', where Y is O or, preferably, NH, and R is a stable linear chain two to six atoms in length having bonds selected from alkyl, alkenyl, ether, thioether, and amino, and is preferably —(CH$_2$)$_3$—. An exemplary compound of this class includes the compound designated herein as "GRN163L A/Link" (see FIG. 7). Other exemplary compounds include compounds corresponding to GRN163L A/Link in which one or more —O—P(O)(S$^-$)— residues in GRN163L A/Link are replaced with —NH—P(O)(S$^-$)— (i.e., phosphorothioate linkages are replaced with NPS linkages).

In another aspect, the invention provides a method of inhibiting adhesion of cells, especially of cancer cells, by contacting the cells with a compound or compounds having a structure represented by O-(x-L)n, as defined above. Preferably, when the oligonucleoside O includes a sequence seven or more nucleobases in length that is complementary to a region of hTR (SEQ ID NO: 1), the compound O-(x-L)n is not a telomerase inhibitor as defined herein. More preferably, the compound O-(x-L)n is not a telomerase inhibitor as defined herein. Various further embodiments of the method include the use of further selected embodiments of the compounds as defined herein.

In a related aspect, the invention provides a method of treating cancer in a patient, by inhibiting adhesion of cancer cells, comprising administering to the patient an effective amount of a compound or compounds having a structure represented by O-(x-L)n, as defined above. Preferably, when the oligonucleoside O includes a sequence seven or more nucleobases in length that is complementary to a region of hTR (SEQ ID NO: 1), the compound O-(x-L)n is not a telomerase inhibitor as defined herein. More preferably, the compound O-(x-L)n is not a telomerase inhibitor as defined herein. Various further embodiments of the method include the use of further selected embodiments of the compounds as defined herein. The compound is provided in a carrier suitable for pharmaceutical use in the patient. In one embodiment, administration of the compound(s) accompanies tumor biopsy or tumor-reductive surgery.

In further related aspects, the invention provides a compound having a structure represented by O-(x-L)n, according to any embodiment as defined above, for use in medicine, and/or for the manufacture of a medicament for treating cancer. The invention also provides a compound having a structure represented by O-(x-L)n, according to any embodiment as defined above, for use in the manufacture of a medicament for inhibiting adhesion or cells, especially cancer cells. Preferably, when the oligonucleoside O includes a sequence seven or more nucleobases in length that is complementary to a region of hTR (SEQ ID NO: 1), the compound O-(x-L)n is not a telomerase inhibitor as defined herein. More preferably, the compound O-(x-L)n is not a telomerase inhibitor as defined herein. Various embodiments of the method include the use of selected embodiments of the compounds as defined herein.

These and other objects and features of the invention will become more fully apparent when the following detailed description of the invention is read in conjunction with the accompanying drawings.

BRIEF DESCRIPTION OF THE DRAWINGS

FIG. 1A: A549-Luciferase cells (A549-Luc cells, 1×$10^5$) were treated with either 1 μM of mismatch control (MM; SEQ ID NO: 3) or GRN163L prior to cell attachment, and phase contrast photomicrographs (20×) were taken after 24, 48, or 72 hours of treatment.

FIG. 1B: Telomeric repeat amplification protocol analysis of telomerase activity (TRAP activity) of A549-luc cells (1×$10^5$) treated prior to cell attachment with either MM or different doses of GRN163L. Lane 1, negative control (lysis buffer); Lanes 2-4, positive controls (H1299 cells (2500, 250 and 25 cells)); Lanes 5-8, 24 hr treatment of MM or GRN163L; Lanes 9-12, 48 hr treatment of MM or GRN163L; Lanes 13-16, 72 hr treatment of MM or GRN163L.

FIGS. 2A-D show the results of experiments demonstrating that GRN163L-induced altered cell morphology is independent of telomerase RNA (hTR) (FIGS. 2A-B) and telomerase activity (2C-D).

FIG. 2A: SUSM-1, VA13 (both hTR negative), and normal BJ cells were treated prior to cell attachment with 1 μM of MM or GRN163L, and phase contrast photomicrographs (20×) were taken after 24 hours of treatment.

FIG. 2B: RT-PCR analysis of hTR levels in SUSM-1, VA13, and VA13hTR cells. (Banding/pixelation in the images is an artifact of the enlargement process.)

FIG. 2C: A549-luc cells were treated prior to cell attachment with 1 μM of 13-mer MM, 13-mer GRN163L, or truncated variants (11-mer, 9-mer and 7-mer) of GRN163L, and phase contrast photomicrographs (20×) were taken after 24 hours of treatment.

FIG. 2D: Twenty-four hour TRAP analysis of A549-luc cells treated prior to cell attachment with 1 or 10 μM of either 13-mer MM or truncated oligomers of GRN163L, respectively. Lane 1, negative control (lysis buffer); Lanes 2-4, positive controls (H1299 cells (2500, 250 and 25 cells)); Lane 5, no treatment; Lanes 6-7, 13-mer MM; Lanes 8-9, 13-mer GRN163L; Lanes 10-11, 11-mer GRN163L; Lanes 12-13, 9-mer GRN163L; Lane 14, 7-mer GRN163L.

FIG. 3A: Immunofluorescent localization of rhodamine-labeled adenoviral hTERT (center column) in A549-luc cells after 6, 16 and 33 days of infection.

FIG. 3B: TRAP analysis of A549-luc cells infected transiently with adenoviral hTERT. Lane 1, negative control (lysis buffer); Lanes 2-4, positive controls (H1299 cells (2500, 250 and 25 cells)); Lane 5, negative control (lysis buffer); Lane 6, A549-luc; Lane 7, A549-luc+adenohTERT 4 days.

FIG. 3C: Quantification of TRAP activity gel, including data for A549-luc+adenohTERT 16 days and A549-luc+adenohTERT 33 days.

FIG. 3D: A549-luc and A549-luc AdhTERT 2 and 3 weeks post-infection were treated prior to cell attachment with 1 μM of MM or GRN163L, and phase contrast photomicrographs (20×) were taken after 24 hours of treatment.

FIG. 4A: A549-luc cells were treated prior to cell attachment (top row) or after overnight attachment (bottom row) with 1 μM MM or GRN163L, and phase contrast photomicrographs (20×) were taken after 24 hours of treatment.

FIG. 4B: Attachment assay quantitation of A549-luc cells grown on plastic or plastic coated with Type I Collagen (1, 6 or 25 μg/ml). Cells were treated for 20 minutes with 1 μM MM or GRN163L, prior to cell attachment (left graph) or after 1 hour attachment (right graph).

FIG. 4C: Spreading assay photomicrographs of A549-luc cells grown on plastic or plastic coated with Type I Collagen (25 μg/ml). Cells were treated for 90 min with 1 μM MM or GRN163L, prior to attachment (left panel) or after 1 hr attachment (right panel).

FIG. 4D: Graphic quantitation of the results shown in FIG. 4C.

FIG. 5A: A549-Luc cells were injected via the tail vein into immunodeficient mice. The animals were administered a single dose of either MM (15 mg/kg) or GRN163L (15 mg/kg) intraperitoneally at the time of cell inoculation. Bioluminescent images (BLI) of the luciferase-expressing A549 cells were recorded at days 13, 20 and 27 of tumor progression.

FIG. 5B: Average BLI signals are depicted graphically.

DETAILED DESCRIPTION OF THE INVENTION

I. Definitions

Figure 1A:
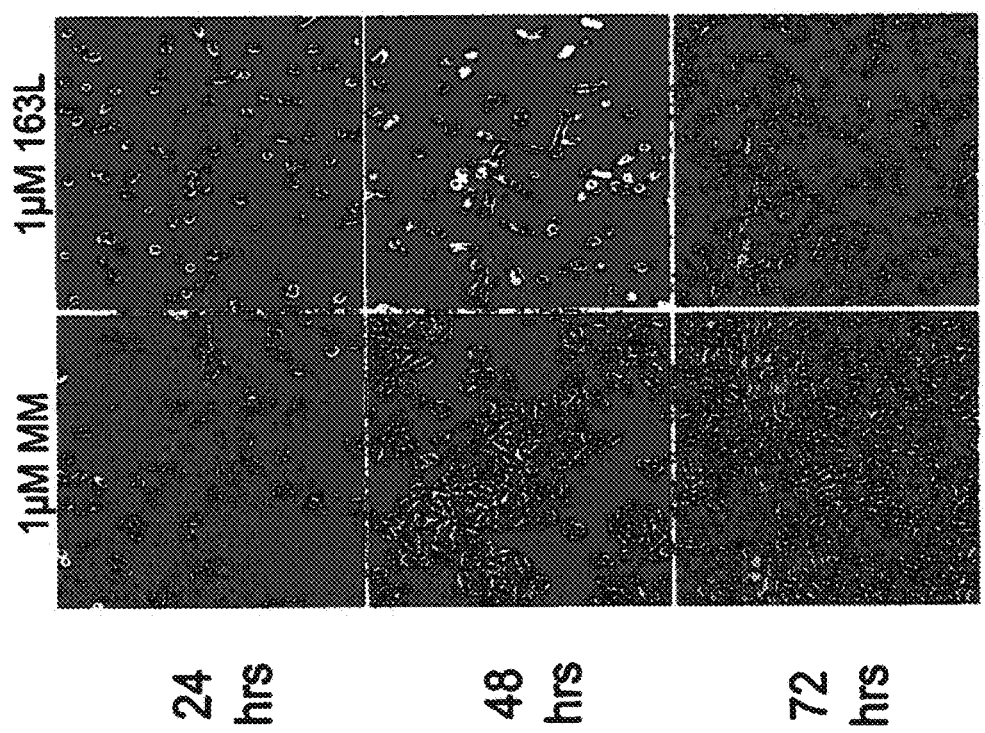
FIGS. 1A-B show morphological alterations and inhibition of telomerase activity induced by GRN163L (SEQ ID NO: 2) in A549-luciferase lung adenocarcinoma cells.

The terms below have the following meanings unless indicated otherwise.

The term "nucleoside" refers to a moiety having the general structure below, where B represents a nucleobase as defined herein, and the 2' carbon may be substituted as described below. When incorporated into an oligomer or polymer, the 3' carbon is further linked to an oxygen or nitrogen atom.

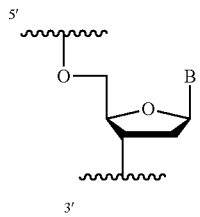

This structure includes 2'-deoxy and 2'-hydroxyl (i.e. deoxyribose and ribose) forms, e.g., as described in Komberg and Baker, DNA Replication, 2nd Ed. (Freeman, San Francisco, 1992), and analogs. Less commonly, a 5'-NH group may be substituted for the 5'-oxygen. "Analogs", in reference to nucleosides, includes synthetic nucleosides having modified nucleobase moieties (see definition of "nucleobase" below) and/or modified sugar moieties, such as 2'-fluoro sugars, and further analogs such as described by Scheit in *Nucleotide Analogs* (John Wiley, New York, 1980). Such analogs are typically designed to enhance binding properties, e.g., stability, specificity, or the like (see e.g. Uhlmann and Peyman, *Chemical Reviews* 90:543-584, 1990).

A "polynucleotide" or "oligonucleoside", which terms are generally used interchangeably herein, refers to an oligomer or polymer of the above-referenced nucleoside moieties, having between 2 and about 200 and preferably between 5 and about 30 such moieties, joined by linkages between their 5' and 3' positions.

These terms include the terms "polynucleotide" or "oligonucleotide", in which the subunits are joined by phosphorus-based linkages two atoms in length between the 5' oxygen and 3' carbon in the structure above, with phosphorus linking the 5' oxygen to a nitrogen or oxygen atom on the 3' carbon. Such linkages include, but are not limited to, phosphodiester ("native" linkage), phosphotriester, methylphosphonate, P3'→P5' phosphoramidate, N3'→P5' phosphoramidate (NP), N3'→P5' thiophosphoramidate (NPS), and phosphorothioate linkages. Such linkages may be the same or different within a molecule. Preferred linkages are NP and NPS linkages, with NPS linkages especially preferred. (Specifically, an "NPS linkage" in the compounds of the invention is the group 3'-NH—P(O)(S—)-5'; an "NP linkage" is the group 3'-NH—P(O)(O—)-5'.) These linkages have the benefits of high hydrolytic stability and resistance to cellular nucleases. In addition, they show much less nonspecific protein binding than exhibited by phosphorothioate linkages.

Use of the term "polynucleoside" or "oligonucleoside" herein includes oligomers or polymers having linkages other than these more conventional linkages, such as described further below.

These terms "oligonucleotide" and "oligonucleoside" also include such polymers or oligomers having modifications, known to one skilled in the art, to the sugar (e.g., 2' substitutions), the base (see the definition of "nucleobase" below), and the 3' and 5' termini.

When a base sequence is represented by a sequence of letters, such as "ATGUCCTG," it is understood that the nucleobases are in 5'→3' order from left to right. Representation of the base sequence of an oligonucleoside in this manner does not imply the use of any particular type of nucleoside subunit or linkage in the oligonucleoside.

A "nucleobase" (or "base") includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA nucleobase.

The term "lipid" encompasses substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. Preferred lipids are hydrocarbons, fatty acids and their derivatives. Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters. The term "hydrocarbon" encompasses compounds that consist only of hydrogen and carbon, joined by covalent bonds. The term encompasses open chain (aliphatic) hydrocarbons, including straight chain and branched hydrocarbons, and saturated as well as mono- and poly-unsaturated hydrocarbons.

The term "substituted" refers to a compound which has been modified by the exchange of one atom or moiety for another, typically substitution of hydrogen by a different atom or moiety.

A compound that is a "telomerase inhibitor" produces a reduction in activity of a telomerase enzyme, preferably by 10%, 25%, 50% or more, when the enzyme is exposed to the compound, as measured in a TRAP assay (as described in Herbert et al., 2002) relative to a medium-only control. Conversely, a compound is "not a telomerase inhibitor" if exposure of the compound to a telomerase enzyme produces no significant reduction in activity of the enzyme (i.e. less than 10%, less than 5%, or no measurable reduction) as measured in a TRAP assay relative to a medium-only control.

II. Anti-Adhesive Effects Observed in Oligonucleotide-Based Telomerase Inhibitors As described above, certain NPS-linked oligonucleotides targeting hTR have proven to be effective inhibitors of telomerase, causing reversible telomerase inhibition and subsequent telomere shortening in human mammary epithelial cells (Herbert et al., 2002). This telomere erosion correlates with the induction of senescence or apoptosis in prostate cancer, multiple myeloma, and non-Hodgkins lymphoma cells and a reduction of tumor growth in myeloma and glioblastoma xenograft models (Asai et al., 2003; Ozawa et al., 2004; Wang et al., 2004).

Lipid modification of the oligonucleotides increases intracellular uptake, inhibition of telomerase, rate of telomere shortening, and growth inhibition and apoptosis in human mammary epithelial cell and hepatoma cell lines, relative to the unconjugated oligonucleotide (Djojosubroto et al., 2005; Herbert et al., 2005).

At the time of the invention, it was generally assumed that a lag phase of therapeutic efficacy (e.g. weeks to months of treatment) would be required for telomerase inhibiting agents to alter cancer cell malignancy (Chen et al., 2003), in view of the mechanism of telomerase inhibition leading to progressive telomere shortening. When a few telomeres became critically short, mitotic catastrophe eventually would result in cell death (Keith et al., 2004).

Therefore, it was of particular interest to the present inventors that, within only 1-2 weeks of treatment with the lipid-conjugated NPS oligonucleotide GRN163L, an A549 lung cancer cell line and an MDA-MB-435 breast cancer cell line exhibited reductions in clonal efficiency, loss of anchorage-dependent growth capabilities, and decreased invasiveness (Dikmen et al., 2005; Gellert et al., 2005a). These changes in cell behavior were much too rapid to correlate with the progressive telomere deletion events observed with the non-conjugated oligonucleotide GRN163 (Akiyama et al., 2003; Asai et al., 2003; Herbert et al., 2005; Ozawa et al., 2004; Wang et al., 2004). Studies showed that critical telomere shortening did not occur in cell culture in the A549 and MDA-MB-435 cell lines until 6-8 weeks of continuous treatment with GRN163L (Dikmen et al., 2005; Gellert et al., 2005a; Gellert et al., 2005b).

However, after only 24 hours of treatment with GRN163L, the A459 cells exhibited morphological alterations indicative of phenotypic changes in cellular adhesion (Example 1; see also Dikmen et al., 2005). After 72 hours of treatment, when the morphological alterations were most prominent (FIG. 1A), an approximately 35% reduction in total cell number was observed when compared to the MM (mismatch sequence; SEQ ID NO: 3) control oligonucleotide-treated cells, with a concomitant 95% reduction in telomerase activity (FIGS. 1B and 1C).

III. Characteristics of Anti-Adhesive Effects

The results described above demonstrate a previously uncharacterized anti-adhesive effect of GRN163L, which may represent a novel anti-metastatic mechanism of action for this and related compounds. The reduction in A549 lung metastases in GRN163L-treated mice may be partially related to the decreased adhesiveness of the A549 cells induced by GRN163L.

Figure 4A:
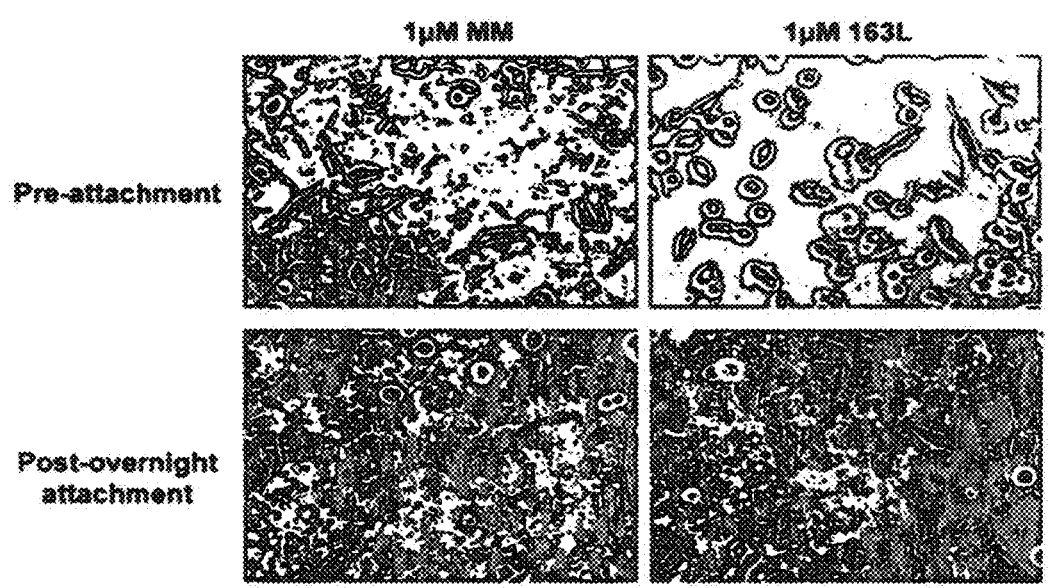
FIGS. 4A-D show GRN163L-induced alteration of A549-luc cell attachment and spreading.
Figure 4B:
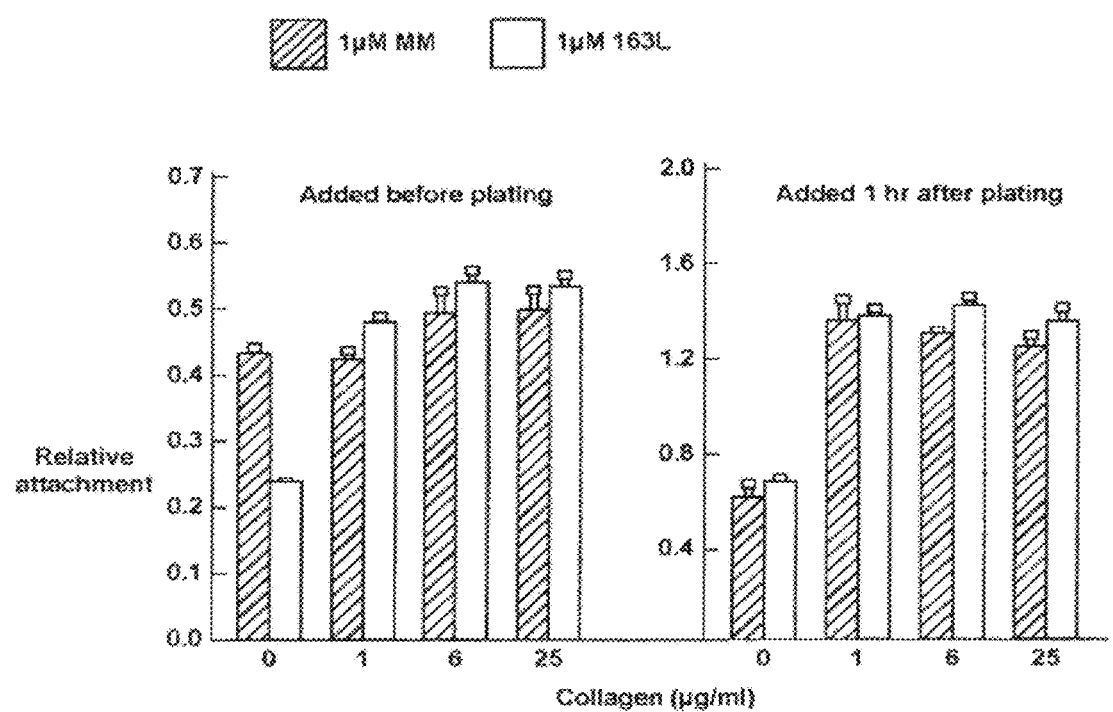
Figure 4C:
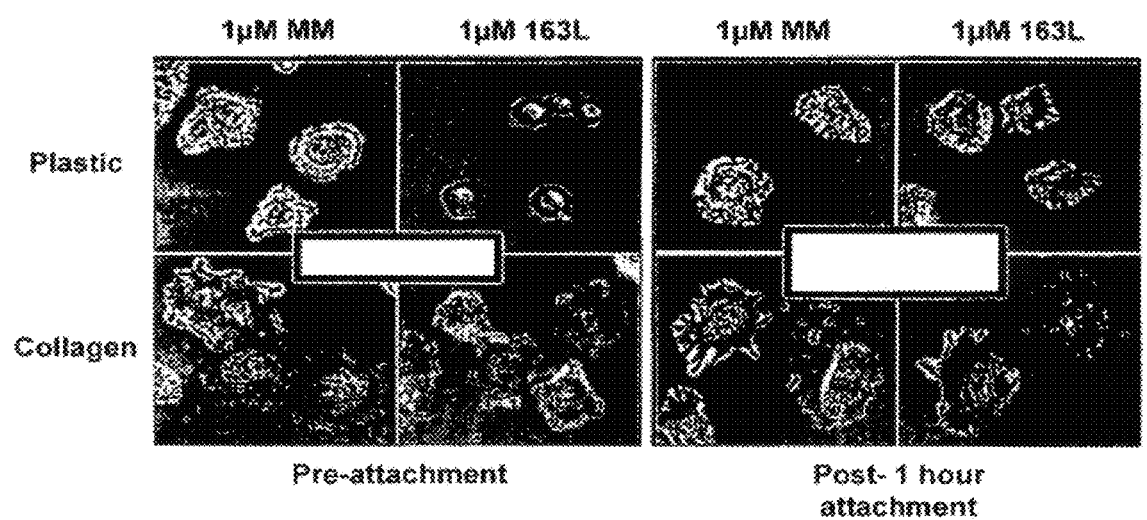
Figure 4D:
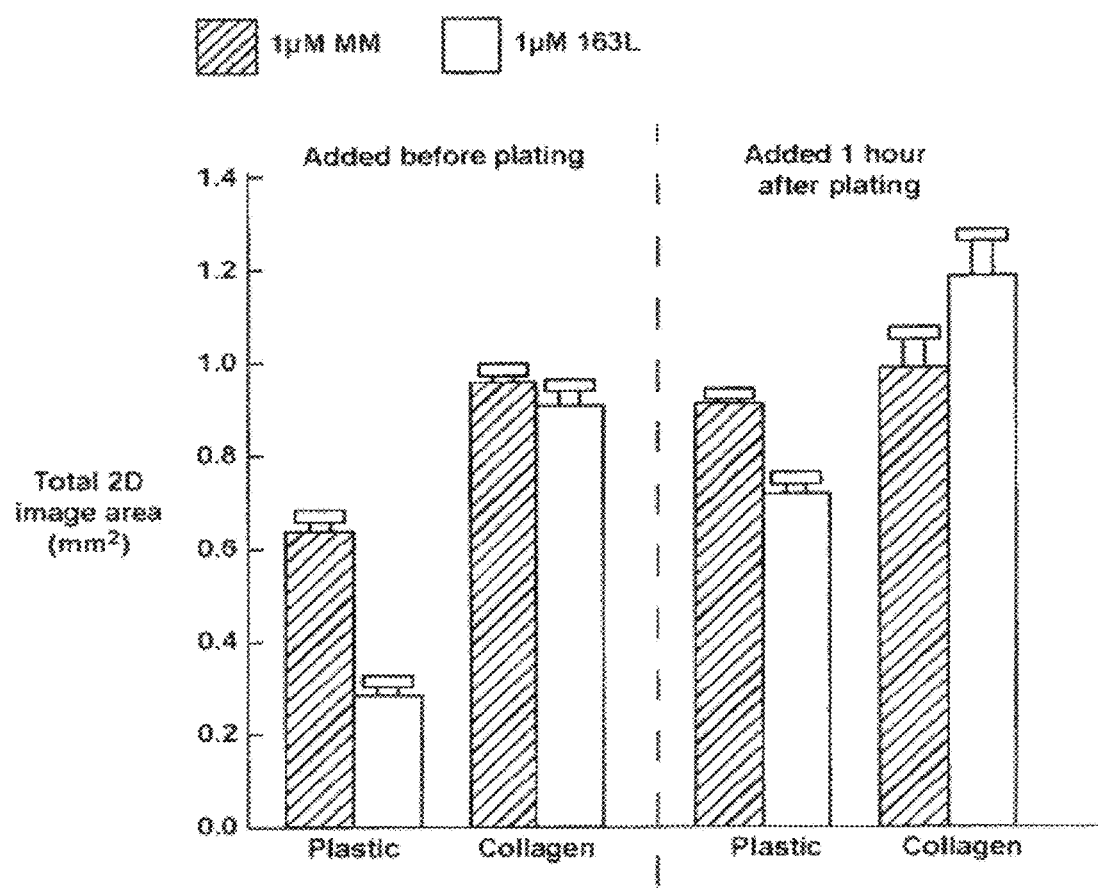

Cell adhesion can be viewed as an intricately orchestrated two-step process, i.e., initial attachment to the substratum and subsequent cell spreading. As described in Example 4, A549-luc cells treated prior to cell attachment with a single dose of 1 µM GRN163L exhibit a 50% reduced ability to attach to plastic substrata (FIG. 4C, left panel) and have incomplete cytoplasmic protrusions coupled with retarded cell flattening after 90 minutes of incubation, whereas cells treated with 1 µM MM-Control appear well spread with numerous lamelipodia (FIG. 4C, left panel). Quantitatively, the GRN163L-treated cells had a 57% reduction in total cell surface area (FIG. 4D) relative to MM-treated cells.

Cells allowed to attach to plastic substrata for 1 hour prior to treatment, however, were more resistant to the anti-cell attachment effect of the drug (FIG. 4B), showing only a 22% reduction in cell spreading between the MM and GRN163L-treated cells (FIGS. 4C and D, right panels). It was found that cell adhesion was altered only when the cells were treated at the time of, or prior to, cell attachment (e.g. within 4 hours of plating). FIG. 4A shows that A549-luc cells allowed to attach to the substrata for several hours were not morphologically altered, relative to control, when treated afterwards with GRN163L (FIG. 4B).

It was also found that coating of wells with type I collagen blocked the GRN163L-induced reduction in cell attachment (FIGS. 4C and D, right side). According to the current study findings, type I collagen may be a potential protein that interacts with GRN163L, at least ex vivo (FIGS. 4B, C and D).

IV. Anti-Adhesive Effects are Independent of Telomerase Inhibition

The present inventors have discovered that a class of compounds defined by certain structural elements, but not necessarily possessing the functional characteristic of inhibiting telomerase, are able to induce cell rounding in cancer cells and inhibit the adherence of the cancer cells to a substrate. That is, the present inventors have discovered that such cellular morphological changes can be effected independent of hTR expression and independent of inhibition of the telomerase holoenzyme. The present invention describes a new class of compounds having such anti-adhesive properties.

Figure 2A:
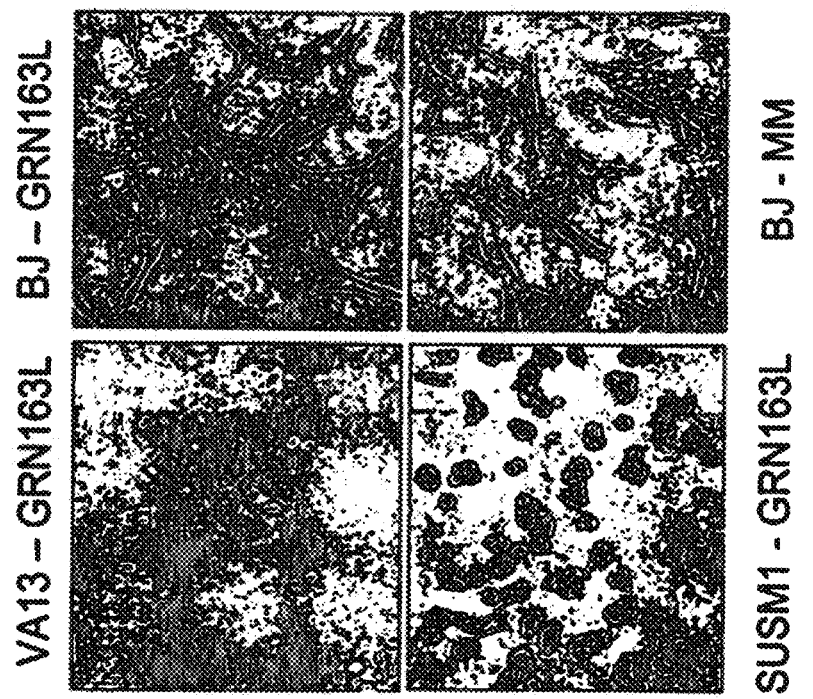

In order to illustrate the invention, two different ALT (telomerase-independent) cell lines (SUSM-1 and VA13) that completely lack hTR RNA expression, but retain the hTR gene (Bryan et al., 1997), were used (Example 2) to show that, even in the total absence of hTR expression, the lipidated NPS oligonucleotide GRN163L alters cell morphology (FIG. 2A). This observation also suggests that further oligonucleotides, as described herein, having these anti-cell adhesive effects may be effective against ALT tumors.

Figure 2B:
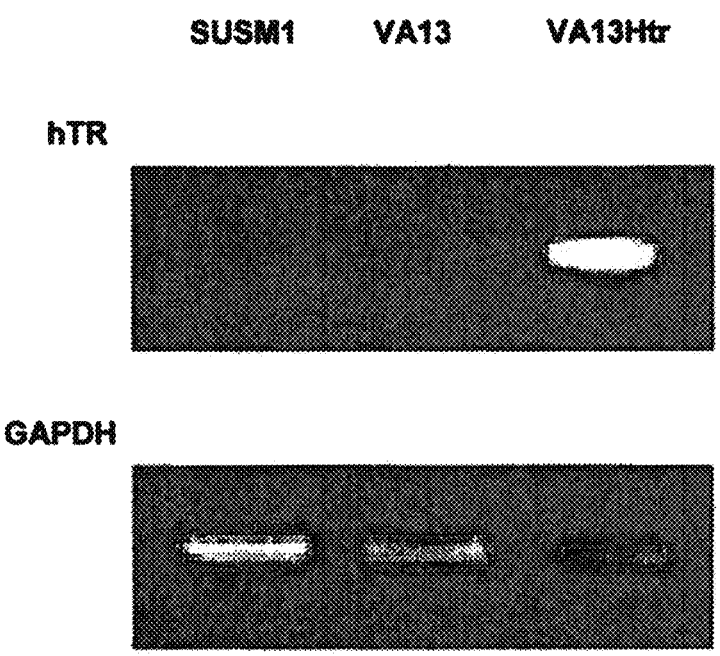
Figure 2D:
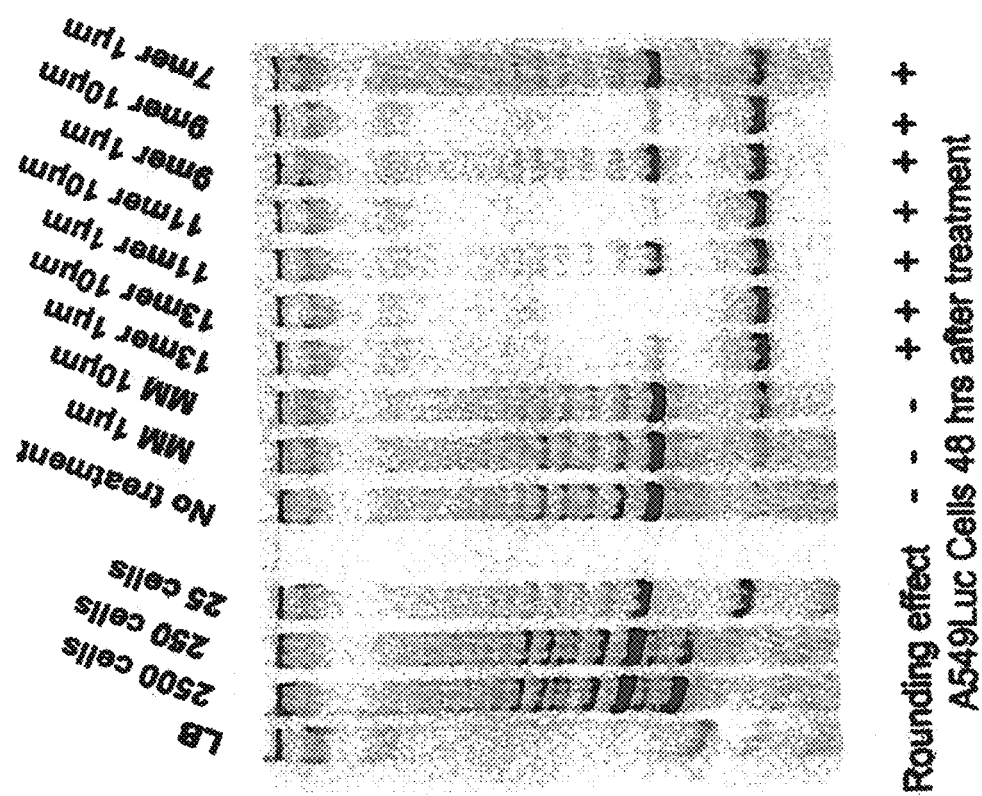

Also tested were truncated versions of the 13-mer GRN163L, including the 11-mer, 9-mer, and 7-mer, which have less of an inhibitory effect on telomerase activity (FIG. 2D). For example, the 7-mer was not an efficient telomerase inhibitor under the experimental conditions used. However, the 7-mer produced rapid changes in A549 cell morphology (FIG. 2C).

The anti-adhesive activity of these compounds also appears to be independent of telomere length in the affected cells (Example 3). To demonstrate this correlation, telomeres in A549 cells were transiently elongated via infection with adenoviral hTERT (FIG. 3). After 3 weeks, when short telomeres were elongated and telomerase activity returned to basal levels (FIG. 3C), the A549 cells were still susceptible to inducement of altered morphology by administration of GRN163L.

These data suggest multiple mechanisms of action of these oligonucleotides in the A549 cells: the well-characterized effects of telomerase inhibition shown, for example, by GRN163L, directly mediated by interaction with the hTR domain of telomerase (Dikmen et al., 2005), and the newly discovered anti-cell adhesive mechanism, which is independent of hTR expression, telomerase inhibition, and telomere length.

V. Structural Features of Anti-Adhesive Invention Compounds

In accordance with the invention, additional oligonucleoside-based agents having anti-adhesive activity are provided. These additional agents, as described further below, include at least a plurality of N3'→P5' thiophosphoramidate (NPS) internucleoside linkages in an oligonucleoside containing at least one G-rich motif. The G-rich motif may consist of three contiguous guanosine residues (GGG) or a pair of G dimers (GG-GG) separated by at most three residues, as described further below. The oligonucleoside is conjugated to a lipid, preferably a lipid which is substantially linear and hydrocarbon-based.

Thus, in one aspect of the invention, compounds are provided which have a structure represented by O-(x-L)n, where:

(a) O is an oligonucleoside moiety comprising a sequence of nucleosides joined by internucleoside linkages, wherein (i) at least 50% of the internucleoside linkages are selected from 3'-NH—P(O)(S⁻)-5' (i.e., N3'→P5' thiophosphoramidate linkages) and 3'-NH—P(O)(S—)—O—R—Y—P(O)(S⁻)-5', where Y is O or, preferably, NH, and R is a stable linear chain two to six atoms in length having bonds selected from alkyl, alkenyl, ether, thioether, and amino; and (ii) the compound includes at least one G-rich sequence motif selected from GGG and GG(W)$_{1-3}$GG, where G is guanosine and W is a nucleoside or the moiety —O—R—, where R is as defined above;

(b) L is a lipid moiety, (c), x is an optional linker group, and (d) n is 1 or 2, and is preferably 1.

In a related aspect, the invention provides compounds having a structure represented by O-(x-L)n, where (a) O is a polynucleoside moiety comprising a sequence of nucleosides joined by internucleoside linkages, wherein (i) at least 50% of said linkages are selected from 3'-NH—P(O)(S⁻)-5' (i.e., N3'→P5' thiophosphoramidate linkages) and 3'-NH—P(O)(S—)—{OR}$_m$—Y—P(O)(S⁻)-5'; where Y is O or, preferably, NH; R is a stable linear chain two to six atoms in length having bonds selected from alkyl, alkenyl, ether, thioether, and amino; and m is 1-3, preferably 1; and (ii) said sequence includes at least one G-rich motif selected from GGG and GG(W)$_{1-3}$GG, containing residues G and/or W, where G is guanosine and W is a nucleoside or the moiety —O—R—, where R is as defined above, and the inter-residue linkages within this motif are N3'→P5' thiophosphoramidate (3'-NH—P(O)(S—)-5') linkages or phosphorothioate (3'-O—P(O)(S—)-5') linkages, and are preferably N3'→P5' thiophosphoramidate linkages;

(b) x is an optional linker group, (c) L is a lipid moiety, and (d) n is 1 or 2, and is preferably 1;

with the proviso that, when said oligonucleoside O includes a sequence seven or more nucleobases in length that is complementary to a region of hTR (SEQ ID NO: 1), the compound O-(x-L)n is not a telomerase inhibitor.

In a further related aspect, compounds of the invention have a structure represented by O-(x-L)n, where:

(a) O is an oligonucleoside moiety comprising a sequence of nucleosides and linkage moieties, wherein (i) at least 50% of the linkage moieties are selected from: 3'-NH—P(O)(S⁻)-5' (i.e., N3' thiophosphoramidate linkages); 3'-NH—P(O)(S—)—{OR}$_m$—Y—P(O)(S⁻)-5'; and 3'-Y—R—O—P(O)(S⁻)-5'; where Y is O or, preferably, NH, R is a stable linear chain two to six atoms in length having bonds selected from alkyl, alkenyl, ether, thioether, and amino; and m is 1-3, preferably 1; and (ii) the compound includes at least one G-rich sequence motif selected from GGG and GG(W)$_{1-3}$GG, containing residues G and/or W, where G is guanosine and W is a nucleoside or the moiety —O—R—, where R is as defined above, and the inter-residue linkages within this motif are selected from phosphorothioate and, more preferably, NPS linkages;

(b) L is a lipid moiety, (c), x is an optional linker group, and (d) n is 1 or 2, and is preferably 1.

The anti-adhesive compounds provided as part of the present invention are characterized in that (i) the oligonucleoside O does not includes a sequence seven or more nucleobases in length that is complementary to a region of hTR (SEQ ID NO: 1) and/or (ii) the compound is not a telomerase inhibitor; that is, exposure of a telomerase enzyme to the compound produces no significant reduction in activity of the enzyme as measured in a TRAP assay, as described in Herbert et al., 2002; see also the Experimental section below. Preferably, at least characteristic (ii) applies; and more preferably, both characteristics (i) and (ii) apply.

A. Selection of O

The term "nucleoside" in the description above corresponds to the structure below, where B is a nucleobase as defined herein:

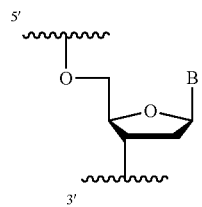

A partial structure of a representative oligonucleoside O is shown below.

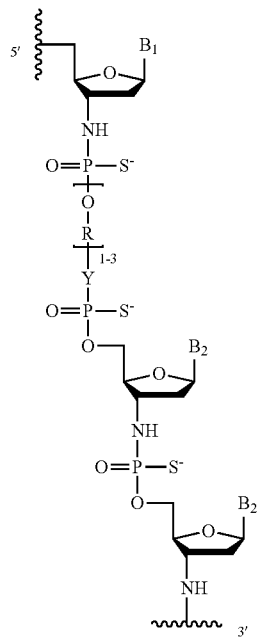

As shown and described, the compound may contain one or more groups —O—R—, referred to herein as abasic groups. The abasic group(s) may occur within the backbone and/or at one or both termini of the oligonucleoside.

Figure 7:
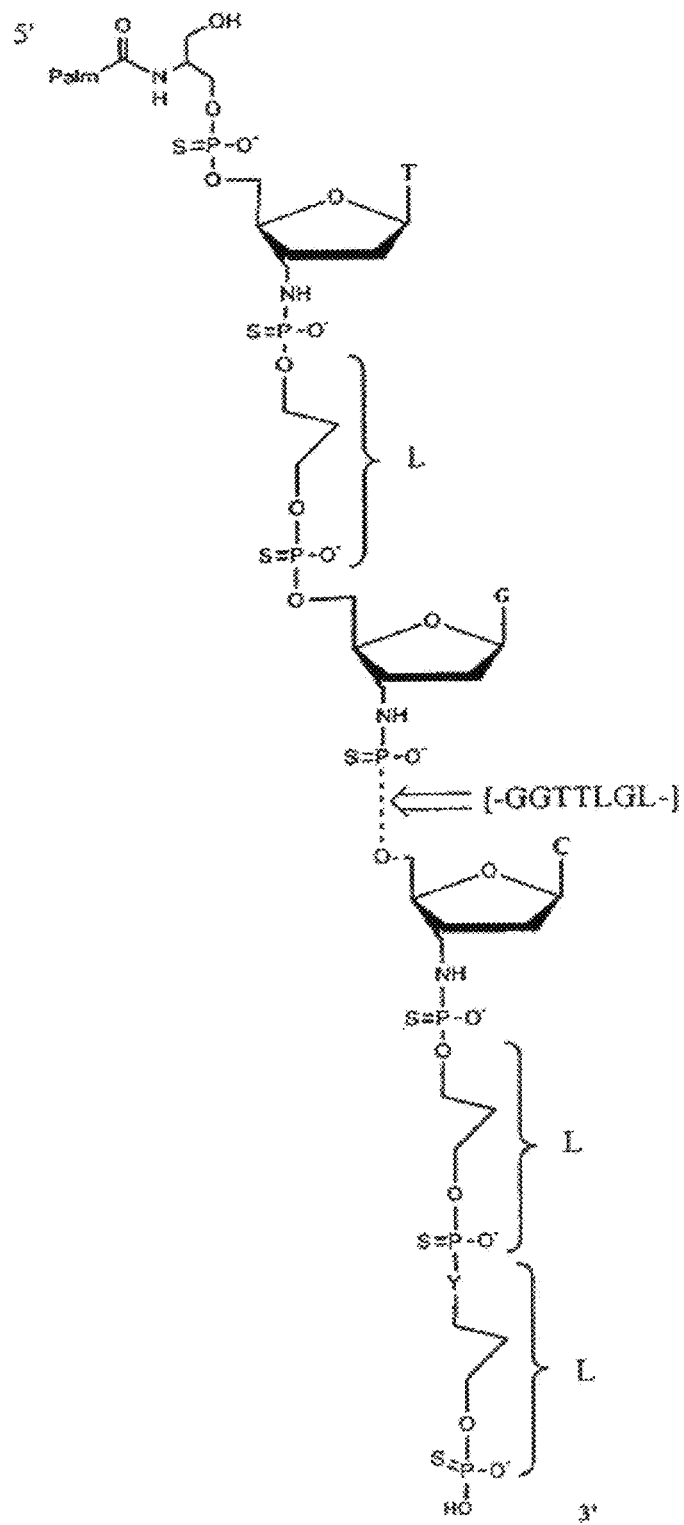
FIG. 7 shows the partial structure of an anti-adhesive compound of the invention designated GRN163L "A/Link", having abasic groups substituted for adenosine nucleosides. In this compound, linkages between adjacent nucleosides (i.e. without intervening abasic groups) are N3'→'P5' thiophosphoramidate (NPS) linkages. (Note that the variable L employed in the Figure does not represent a lipid moiety as in the general structural definition O-(x-L)n.)

FIG. 7 depicts an exemplary compound designated "GRN163L A/Link", in which each A nucleoside in the compound GRN163L, described above, is replaced by —Y—(CH$_2$)$_3$—O—P(O)(S—)—, where Y is O or NH. (Note that the nucleosides may include ribonucleosides or analogs as defined above, as well as the deoxyribonucleosides depicted in the above structure.)

When an abasic group —O—R— is present as an embodiment of W in a GG(W)$_{1-3}$GG motif, the variable Y in the adjacent phosphorus-containing linkage is preferably NH, such the adjacent phosphorus-containing linkage is an NPS linkage. When the abasic group —O—R— occurs elsewhere in the compound, Y is O or, preferably, NH.

As stated above, R (in the group —O—R—) is a stable linear chain two to six atoms in length having bonds selected from alkyl, alkenyl, ether, thioether, and amino. Accordingly, the chain contains (exclusive of hydrogen) carbon atoms and optionally oxygen, nitrogen, or sulfur atom(s). Preferably, the chain contains (exclusive of hydrogen) only carbon and oxygen atoms (i.e., alkyl and ether linkages) or only carbon atoms (i.e. alkyl and/or alkenyl linkages). In one embodiment, R is —(CH$_2$)$_n$—, where n is 3 to 5, preferably where n is 3. In this embodiment, the spacing between phosphorus-based linkages in the compound is approximately the same as in a conventional oligonucleotide. Nonetheless, oligonucleoside compounds containing these abasic groups can have greatly reduced hybridizing ability; see the description of the compound "163L A/Link" below. Thus, compounds containing more than one or two such groups per about ten residues are not expected to be telomerase inhibitors even when they have sequence regions complementary to hTR.

The oligonucleoside O preferably contains a sequence motif of at least three consecutive guanosine (G) nucleosides directly linked by NPS linkages. Alternatively or in addition, it may contain a sequence motif of two sets of two consecutive guanosine nucleosides (G dimers), each dimer linked by an NPS linkage, where the dimers are themselves linked by 0-3 nucleosides and/or abasic groups —OR— as defined above, and these groups (indicated by W) are likewise joined by NPS linkages.

As noted above, at least 50% of the internucleoside linkages in O are selected from NPS linkages and 3'-NH—P(O)(S—)—{OR}$_m$—Y—P(O)(S$^-$)-5', where m is preferably 1, such that the latter represents an abasic group and flanking phosphorus-based groups. Preferably, at least 75%, more preferably at least 90%, and most preferably all of the linkages in O are selected from these two classes.

Any remaining internucleoside linkages (i.e., those not selected from these two classes) are typically other phosphorus-based linkages two atoms in length, with phosphorus linking the 5' oxygen (or, less commonly, a 5' nitrogen) to a nitrogen or oxygen atom on the 3' carbon. Linkages resistant to endogenous nucleases are preferred. Such linkages include, but are not limited to, methylphosphonate, P3'→P5' phosphoramidate, N3'→P5' phosphoramidate (NP), and phosphorothioate (PS) linkages. Of these, most preferred are 3'-NH—P(O)(O$^-$)-5' (NP) linkages.

The sum of nucleosides and abasic groups —OR— in the oligonucleoside O typically ranges from 5 to about 30, preferably from 5 to about 20, and more preferably from 7 to about 15. The ratio of nucleosides to abasic groups can vary but is preferably 1:1 or greater. The total number of nucleosides is at least three, in order to provide the sequence motifs described above. Preferably, O contains at least three, more preferably at least five, consecutive nucleosides. In selected embodiments, O contains no more than fifteen, preferably no more than twelve, and more preferably no more than ten, consecutive nucleosides. The consecutive nucleosides are preferably NPS- or NP-linked; more preferably, the nucleosides are NPS-linked.

B. Selection of L

Lipidation of N3'→P5' thiophosphoramidate oligonucleotides has been shown to provide superior cellular uptake properties and pharmacokinetics; see, for example, US Pubn. No. 2005/0113325, which is incorporated herein by reference.

The lipid component L may be any lipid or lipid derivative that provides enhanced cellular uptake compared to the unmodified oligonucleoside. Preferred lipids are linear hydrocarbons, saturated or unsaturated, fatty acids, and fatty acid derivatives, such as fatty amides. The length of the hydrocarbon chain is preferably $C_{14}$-$C_{22}$, more preferably $C_{16}$-$C_{18}$.

Preferred examples of saturated hydrocarbons (alkanes) are listed below:

| Systematic name | Carbon chain |
| --- | --- |
| Tetradecane | $C_{14}H_{30}$ |
| Pentadecane | $C_{15}H_{32}$ |
| Hexadecane | $C_{16}H_{34}$ |
| Heptadecane | $C_{17}H_{36}$ |
| Octadecane | $C_{18}H_{38}$ |
| Nonadecane | $C_{19}H_{40}$ |
| Eicosane | $C_{20}H_{42}$ |

Mono- and poly-unsaturated forms (alkenes and polyenes, such as alkadienes and alkatrienes) of hydrocarbons may also be selected, with compounds having one to three double bonds being preferred, although compound having more double bonds may be employed. Alkynes (containing one or more triple bonds) and alkenynes (triple bond(s) and double bond(s)) may also be utilized.

Other suitable lipid components include simple fatty acids and fatty acid derivatives. Fatty acids and their derivatives may be fully saturated or mono- or poly-unsaturated. The length of the hydrocarbon chain is preferably $C_{14}$-$C_{22}$, more preferably $C_{16}$-$C_{18}$. Preferred examples of saturated fatty acids are listed below:

| Systematic name | Trivial name | Carbon chain |
| --- | --- | --- |
| Tetradecanoic | myristic | 14:0 |
| Hexadecanoic | palmitic | 16:0 |
| Octadecanoic | stearic | 18:0 |
| Eicosanoic | arachidic | 20:0 |

Mono- and poly-unsaturated forms of fatty acids may also be employed, with compounds having one to three double bonds being preferred, although compounds having more double bonds may also be employed. Fatty acids with one or more triple bonds in the carbon chain, as well as branched fatty acids, may also be employed in the compounds of the invention. Examples of common mono- and poly-unsaturated fatty acids that may be employed include:

| Systematic name | Trivial name | Carbon chain |
| --- | --- | --- |
| Cis-9-hexadecanoic | palmitoleic | 16:1 (n - 7) |
| Cis-6-octadecanoic | petroselinic | 18:1 (n - 12) |
| Cis-9-octadecanoic | oleic | 18:1 (n - 9) |
| 9,12-octadecadienoic | linoleic | 18:2 (n - 6) |
| 6,9,12-octadecatrienoic | gamma-linolenic | 18:3 (n - 6) |
| 9,12,15-octadecatrienoic | alpha-linolenic | 18:3 (n - 3) |
| 5,8,11,14-eicosatetraenoic | arachidonic | 20:4 (n - 6) |

Typically, one or two lipid components L are utilized (n=1 or 2). Preferably, n=1. Where more than one L component is linked to the O component, each L component is independently selected.

It will be appreciated that compounds of the invention described as having a specified hydrocarbon as the L moiety and compounds described as having a specified fatty acid (with the same number of carbon atoms as the specified hydrocarbon) are closely related and differ in structure only in the nature of the bond that joins the L moiety to the oligonucleoside G, which in turn is a result of the synthesis procedure used to produce the conjugated compound. For example, when compounds are synthesized having the L moiety conjugated to the 3'-amino terminus of an oligonucleoside, the use of the aldehyde form of a fatty acid (a fatty aldehyde) as the starting material results in the formation of an amine linkage between the lipid chain and the oligonucleoside, such that the lipid group appears as a hydrocarbon. In contrast, use of the carboxylic acid, acid anhydride or acid chloride forms of the same fatty acid results in the formation of an amide linkage, such that the lipid group appears as a fatty acid derivative, specifically in this instance a fatty amide (as noted in the definitions section above, for the sake of simplicity, the term "fatty acid" when describing the conjugated L group is used broadly herein to include fatty acid derivatives, including fatty amides).

C. Selection of x

The linkage between the O and L components may be a direct linkage, or it may be via an optional linker moiety, x. The linker group may serve to facilitate the chemical synthesis of the compounds (discussed in the Experimental section below). Whether or not a linker group is used to mediate the conjugation of the O and L components, there are multiple sites on the oligonucleoside component O to which the L component(s) may be conveniently conjugated. Suitable linkage points include the 5' and 3' termini, one or more sugar rings, the internucleoside backbone and the nucleobases of the oligonucleoside. Typically, the L moiety is attached to the 3' or 5' terminus of the oligonucleoside.

If the L component is to be attached to the 3' terminus, the attachment may be directly to the 3' substituent, such as a 3'-amino group or 3'-hydroxy group. Alternatively, the L moiety may be linked via a 3'-linked phosphate group. If the L moiety is to be linked to the 5' terminus, it is typically attached through a 5'-linked phosphate group.

Attachment to a base on the oligonucleoside may through any suitable atom, for example to the $N^2$ amino group of guanosine.

Examples of preferred linker groups x include amino glycerol and O-alkyl glycerol-type linkers, which can be depicted, respectively, by the generic structures:

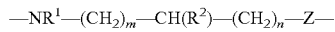

and

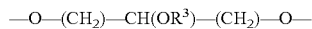

where $R^2$=H, OH, $NH_2$ or SH; Z=O, S or $NR^1$; $R^1$, $R^3$=H or alkyl; and n and m are independently integers between 1-18. Specific examples of suitable linkers are an aminoglycerol linker, in which $R^2$=OH, Z=O, and m and n are each 1 (formula I); a bis-aminoglycerol linker, in which $R^2$=OH, Z=NH, and m and n are each 1 (formula I); and an O-alkyl glycerol linker, in which $R^3$=H (formula II).

In one exemplary structure, the lipid L, as a fatty acid amide, is conjugated through the terminal 3' amino group of an oligonucleoside. In a further exemplary structure, the lipid moiety is a fatty acid amide, such as a palmitoyl amide, conjugated through an aminoglycerol linker to the 5' thiophosphate group of an oligonucleoside, as shown in the Examples below.

VI. Data Showing Anti-Adhesive Properties of the Compounds

Data shown in Table 1 below were collected using 1 µM of the designated compounds, administered prior to cell attachment. Altered adhesion of A549-luc cells (human lung carcinoma) was determined after 24 hrs, and TRAP activity was measured 72 hours post addition, unless otherwise indicated. As noted above, the oligonucleotide GRN163 is a NPS-linked oligonucleotide having the sequence shown as SEQ ID NO: 2 (row 2 of table), and the conjugated oligonucleotide GRN163L includes a palmitoyl amide linked to the 5' terminus via an aminoglycerol linker (see US Pubn. No. 2005/0113325).

As shown, the non-lipidated oligonucleotide (row 3 of table) had no observable affect on cell adhesion. With respect to the type of lipid, lipids which are substantially linear and hydrocarbon-based appeared, on the basis of this data, to be more effective than fluorinated or non-linear lipids, such as PTFE ("Teflon") or cholesterol, respectively. The oligonucleotide GRN163 conjugated with the latter lipids did show anti-adhesive activity, however, at higher concentrations (10 µM) (data not shown).

The data further show that the fully phosphoramidate (NP)-linked oligonucleotides tested did not alter cell adhesion, suggesting that the thio-containing (NPS) linkages are an important factor in anti-adhesive activity. All of the remaining compounds in the Table have fully NPS-linked oligonucleosides.

As shown in FIGS. 1-4, the mismatch compound (MM) (SEQ ID NO: 3), which differs from GRN163L by the lack of three contiguous guanine residues, did not alter cell adhesion. In corroboration with this finding are data collected using truncated versions of GRN163L (11-mer, 9-mer and 7-mer), all of which altered cell adhesion to the same extent as the full length 13-mer (even though the shorter oligos only weakly inhibit telomerase), and all of which retain the triple-G motif.

Further oligonucleotides having a sequence of four guanosine nucleobases (SEQ ID NOs: 6 and 7), in accordance with the invention, were prepared as NPS oligonucleotides modified with a lipid group (5'-palmitoyl). These compounds, which do not inhibit telomerase, were found to have an anti-adhesive effect. On the other hand, oligonucleotides designated SEQ ID NO: 4 and 5, which lack the triple-G motif, did not alter the adhesive ability of the A549 cells.

Figure 6A:
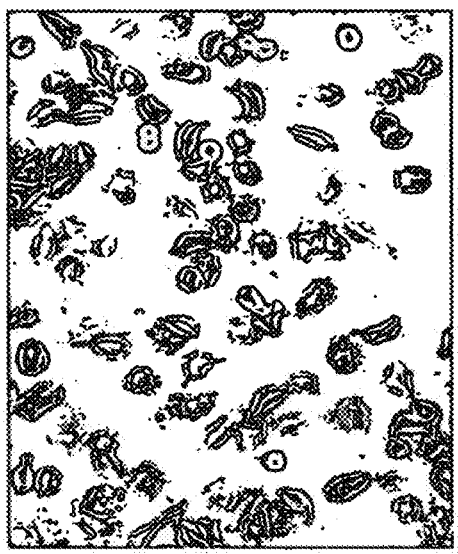
FIGS. 6A-6H show morphological alterations of A549-Luc cells treated with various NPS-linked lipid-conjugated oligonucleoside compounds, in comparison with controls (6A, no treatment; 6B, mismatch control (SEQ ID NO: 3); 6C, GRN163L (SEQ ID NO: 2). The compounds were added to media immediately after plating the cells and incubated for 24 hours.
Figure 6B:
Figure 6C:
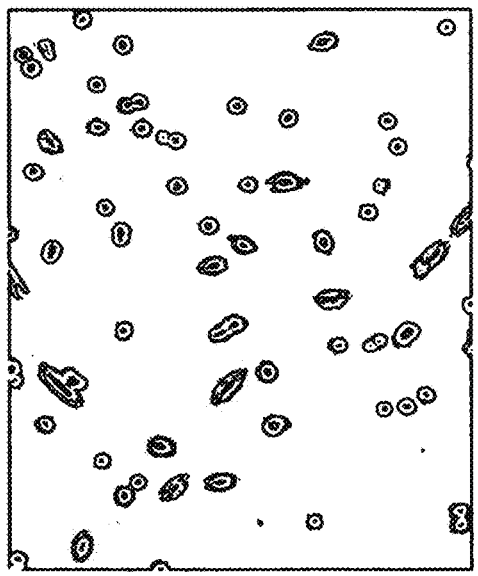
Figure 6D:
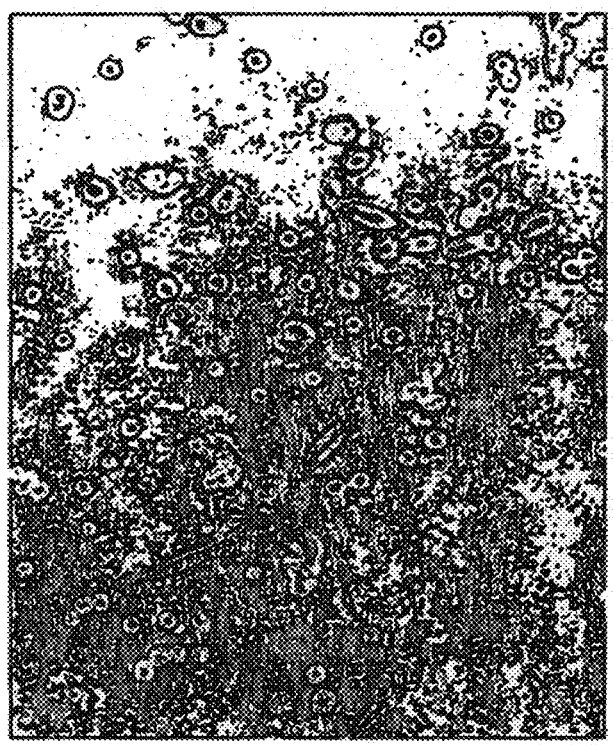
Figure 6E:
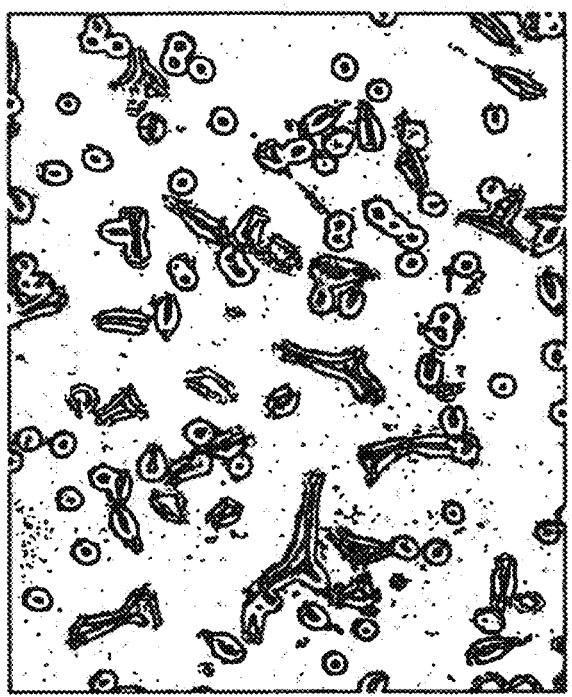

Other oligonucleosides having NPS linkages and a G-rich motif, in accordance with the invention, were also shown to have anti-adhesive activity (see FIGS. 6A-6H). These include the NPS oligonucleotide compound having SEQ ID NO: 8, which includes four GG dimers separated by one or two other nucleotides (FIG. 6E).

Figure 6F:
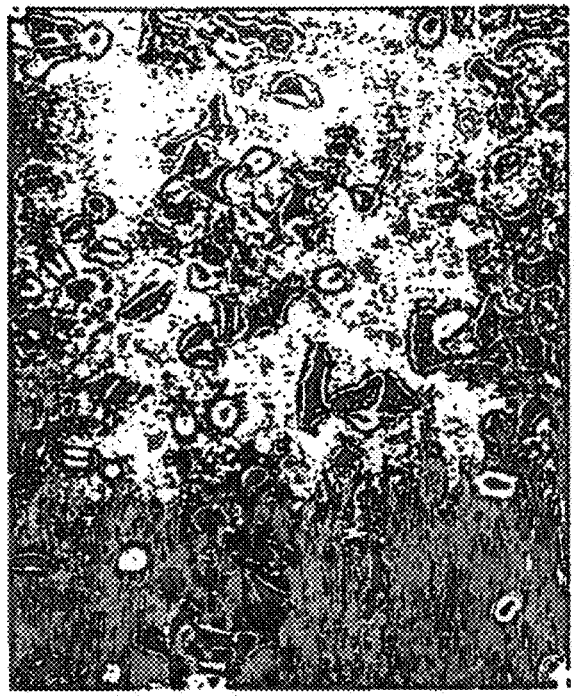
Figure 6G:
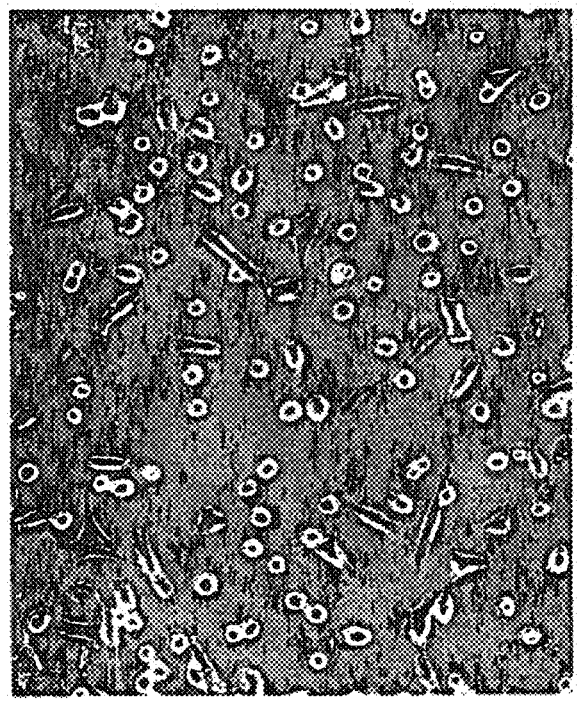

Substitution of methylcytidine for cytidine ("163L-5Me-Cyt"), riboadenosine for deoxyriboadenosine ("163L-2'OH rA"), and ribo sugars for all deoxyribo sugars ("163L-ribo") in GRN163L did not affect anti-adhesive activity (see FIGS. 6D, 6F, 6G).

Figure 6H:

The final compound in Table 1, "163L A/Link", of which the partial structure is shown in FIG. 7, includes an abasic group, as shown, in place of every adenosine nucleoside in GRN163L. This compound is not a telomerase inhibitor, and it does not form stable duplexes with complementary RNA or DNA at body temperature; i.e. $T_m$<37° C. However, it showed significant anti-adhesive activity (FIG. 6H).

Compounds including such abasic groups (i.e. —O—R— as defined herein) and at least one G-rich motif are particularly preferred embodiments of the invention. The number of nucleosides relative to abasic groups is typically 1:1 or more, with typical ratios including 3:2, 2:1, 3:1, 4:1, or 5:1. The compound may also contain more abasic groups than nucleosides, as long as at least one G-rich motif is present. In selected embodiments, the compound does not form stable duplexes with complementary RNA or DNA at body temperature; i.e. $T_m < 37°$ C.

As noted above, the data reported below were obtained in A549-luc (human lung carcinoma) cells. Other cell lines were tested, and the phenomenon did show some cell line dependence. For example, anti-adhesive activity was observed in the majority of, but not all, breast cancer cell lines tested, and no significant activity was observed in T24 (bladder) cells.

It was also shown that in vivo intraperitoneal administration of GRN163L at the time of cell inoculation results in a reduction in A549-luc lung cancer metastasis, as determined by bioluminescence imaging (Example 5). This result suggests that the anti-metastatic effect of GRN163L on A549 may be related, in part, to the heretofore unknown anti-cell adhesive effects of these oligonucleotide agents.

The anti-adhesive action of these compounds can be utilized by administration at the time of tumor biopsy or tumor-reductive surgery. It has been suggested that fine-needle aspiration may stimulate tumor dissemination through the needle track via the mechanical exfoliation of cancer cells (Sawabata et al., 2000). Thus, a single dose of

TABLE 1

| Oligo | Sequence (5' to 3') | Lipid | G-rich motif | TRAP inhibition[a] | Adhesion alteration[b] |
|---|---|---|---|---|---|
| 163L (SEQ ID NO: 2) | TAG GGT TAG ACA A | 5'-palm | Yes | Yes | Yes |
| Mismatch (MM) (SEQ ID NO: 3) | TAG GTG TAA GCA A | 5'-palm | No | No | No |
| 163-13mer | TAG GGT TAG ACA A | none | Yes | No | No |
| 163L-11mer | GTT AGG GTT AG | 5'-palm | Yes | Yes | Yes |
| 163L-9mer | GGG TTA GAC | 5'-palm | Yes | Yes | Yes |
| 163L-7mer | GGG TTA G | 5'-palm | Yes | Moderate | Yes |
| 163-oleic | TAG GGT TAG ACA A | 5'-oleic | Yes | Yes | Yes |
| 163-PTFE | TAG GGT TAG ACA A | 5'-$CF_3(CF_2)n$ | Yes | Moderate | No |
| 163-chol | TAG GGT TAG ACA A | 5'-cholesterol | Yes | Moderate | No |
| 163L NP | TAG GGT TAG ACA A | 5'-palm | Yes | No | No |
| 163-oleic NP | TAG GGT TAG ACA A | 5'-oleic | Yes | No | No |
| SEQ ID NO: 4 | CGT ACC ACG CTC GCT A | 5'-palm | No | NA | No |
| SEQ ID NO: 5 | CTA GAC TCG GAC CCT C | 5'-palm | No | NA | No |
| SEQ ID NO: 6 | AAC GTT GAG GGG CAT | 5'-palm | Yes | No | Yes |
| SEQ ID NO: 7 | AAC GAG TTG GGG CAT | 5'-palm | Yes | No | Yes |
| SEQ ID NO: 8 | GTG GAA GGC GGC AGG | 5'-palm | Yes | Yes | Yes |
| 163L-5MeCyt | TAG GGT TAG AC$^{Me}$A A | 5'-palm | Yes | n.d. | Yes |
| 163L-2'OH rA | TrAG GGT TrAG rACrA rA | 5'-palm | Yes | n.d. | Yes |
| 163L-ribo | r(TAG GGT TAG ACA A) | 5'-palm | Yes | n.d. | Yes |
| 163L "A/Link" | TLG GGT TLG LCL L$^c$ | 5'-palm | Yes | No | Yes |

[a] 24 hr TRAP inhibition with 1 µM compound.
[b] Cells treated prior to attachment with 1 µM compound.
[c] L = 5'-O-$(CH_2)_3$-O-P(O)(S-)-3' or 5'-NH-$(CH_2)_3$-O-P(O)(S-)-3'. Compound tested is as shown in FIG. 7, where Y=O (at 3' terminus) and linkages not explicitly shown are NPS linkages.
(Note that the variable L in this instance does not represent a lipid moiety as in the general structural definition O-(x-L)n.)

VII. In Vivo Activity

The ability of the described anti-adhesive compounds to reduce cell attachment and hasten cell spreading was shown to reduce tumor cell seeding in vivo, as was manifested by a diminished tumor burden in experimental nude mouse models. A single intraperitoneal dose of GRN163L (15 mg/kg) resulted in a reduction in the colonization of A549-luc cells into mice lungs, as shown in Example 5.

GRN163L, or another anti-adhesive compound as described herein, may have a therapeutic effect by preventing the re-attachment and re-colonization of any disseminated tumor cells, and may possibly prevent malignant spread. Pleural carcinosis has been also been reported after the excision of malignant lung tumors (Buhr et al., 1995; Downey et al., 1996). Therefore, in the case of minimal residual disease, post-cytoreductive surgery, GRN163L or another anti-adhesive compound as described herein, may also be efficacious in hastening the maturation of circulating and disseminated tumor cells.

VIII. Administration for Cancer Therapy

The therapeutic protocol for administering the lipid-conjugated oligonucleosides described herein will depend on various factors including, but not limited to, the type of cancer, the age and general health of the patient, and the aggressiveness and stage of disease progression. In particular, the anti-adhesive action of these compounds can be utilized at the time of tumor biopsy or tumor-reductive surgery. It has been suggested that fine-needle aspiration may stimulate tumor dissemination through the needle track via the mechanical exfoliation of cancer cells (Sawabata et al., 2000). Thus, a single dose of GRN163L, or another anti-adhesive compound as described herein, may have a therapeutic effect by preventing the re-attachment and re-colonization of any disseminated tumor cells, and may possibly prevent malignant spread. Pleural carcinosis has been also been reported after the excision of malignant lung tumors (Buhr et al., 1995; Downey et al., 1996). Therefore, in the case of minimal residual disease, post-cytoreductive surgery, GRN163L or another anti-adhesive compound as described herein may also be efficacious in hastening the maturation of circulating and disseminated tumor cells.

In general, treatment of all carcinoma and hematological malignancy types is contemplated. In selected embodiments, the target disease comprises a solid tumor; in other embodiments, the target disease comprises a hematological malignancy. Other preferred targets include small cell lung, non small cell lung, esophageal, head and neck, and stomach cancers.

The oligonucleoside may be administered in conjunction with a conventional chemotherapeutic agents, either sequentially or simultaneously. Multiple treatments may be administered, at intervals of 2-3 days to a week. An exemplary course of treatment involves multiple doses, determined by clinical compliance criteria and/or preclinical or clinical data supporting dose optimization strategies to augment efficacy or reduce toxicity. The time between dosages may be for a period from about 1-6 hours, to about 6-12 hours, to about 12-24 hours, to about 1-2 days, to about 1-2 wk or longer following the initiation of treatment. During a course of treatment, the need to complete the planned dosings may be re-evaluated.

The compound(s) may be administered by direct injection of a tumor or its vasculature. Alternatively, the tumor may be infused or perfused with the therapeutic compound(s) using any suitable delivery vehicle. Systemic administration may also be performed. Continuous administration may be applied where appropriate; for example, where a tumor is excised and the tumor bed is treated to eliminate residual, microscopic disease. Delivery via syringe or catheterization is preferred. Such continuous perfusion may take place for a period from about 1-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs.

The compound is administered to a subject, such as a human patient, in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor specific markers such as serum PSA), and improvement in quality of life (as determined by clinical assessment, e.g., Karnofsky score), increased time to progression, disease-free survival and overall survival.

The amount of agent per dose and the number of doses required to achieve such effects will vary depending on many factors including the disease indication, characteristics of the patient being treated, and mode of administration. Typically, the formulation and route of administration will provide a local concentration at the disease site of between 1 µM and 1 nM of each agent. The physician will be able to vary the amount of the compounds, the carrier, the dosing frequency, and the like, taking into consideration such factors as the particular neoplastic disease state and its severity; the overall condition of the patient; the patient's age, sex, and weight; the mode of administration; the suitability of concurrently administering systemic anti-toxicity agents; monitoring of the patient's vital organ functions; and other factors typically monitored during cancer chemotherapy. In general, the compound is administered at a concentration that affords effective results without causing excessive harmful or deleterious side effects.

As discussed above, the anti-adhesive action of these compounds as described herein can particularly be utilized by administration at the time of tumor biopsy or tumor-reductive surgery, in order to prevent the re-attachment and re-colonization of any disseminated tumor cells, and thereby prevent malignant spread.

IX. Formulations

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The composition may be administered topically as a solution, cream, or lotion, by formulation with pharmaceutically acceptable vehicles containing the active compound. The compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the oligonucleosides of the present invention may include carriers, lubricants, diluents, thickeners, flavoring agents, emulsifiers, dispersing aids or binders. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

While the lipid-conjugated oligonucleosides described herein have superior characteristics for cellular and tissue penetration, these and other compounds may be formulated to provide further benefit in this area, e.g. in liposome carriers. The use of liposomes to facilitate cellular uptake is described, for example, in U.S. Pat. Nos. 4,897,355 and 4,394,448, and numerous publications describe the formulation and preparation of liposomes. The compounds can also be formulated with additional penetration/transport enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, acylcholines, mono- and di-glycerides and physiologically acceptable salts thereof (i.e., oleate, laurate, caprate, myristate, palmitate, stearate, linoleate, etc.).

EXPERIMENTAL

The following examples illustrate but are not intended in any way to limit the invention.
Materials and Methods
Cell Culture and Morphological Analysis Human non-small-cell lung adenocarcinoma cells (A549) were obtained from ATCC (Manassas, Va.) and were grown in X media (4:1 mixture of Dulbecco's Modified Eagle's Medium:Medium 199) supplemented with 10% cosmic calf serum (HyClone, Logan, Utah) without antibiotics at 37° C. under 5% CO2. A549 cells that express lentivirally delivered luciferase (A549-luc) were generated as previously described (Dikmen et al., 2005). BJ (normal skin fibroblasts), SUSM-1 (4-nitroquinoline (4NQO)-immortalized liver fibroblasts) and VA13 (SV40-immortalized lung fibroblasts) were all obtained from ATCC.

For morphological analyses, 1-3×10⁵ cells were seeded into 10 cm² culture dishes and 1 µM of MM or GRN163L were added directly to the dish prior to cell attachment. Twenty-four to 72 hours later representative phase-contrast micrographs were taken using an inverted Zeiss Axiovert 200M microscope equipped with an AXIO Cam MRM REV2 camera attached with a C-Mount 0.63× adaptor at 20× magnification.

Synthesis and Lipid Conjugation of Oligonucleoside N3'→P5' Thiophosphoramidates

These compounds may be prepared as described, for example, in McCurdy et al., *Tetrahedron Letters* 38:207-210 (1997) or Pongracz & Gryaznov, *Tetrahedron Letters* 49:7661-7664 (1999). The starting 3'-amino nucleoside monomers may be prepared as described in Nelson et al., *J. Org. Chem.* 62:7278-7287 (1997) or by the methods described in Gryaznov et al., US Appn. Pubn. No. 2006/0009636.

A variety of synthetic approaches can be used to conjugate a lipid moiety L to an oligonucleoside, depending on the nature of the linkage selected; see, for example, Mishra et al., *Biochim. et Biophys. Acta* 1264:229-237 (1995), Shea et al., *Nucleic Acids Res.* 18:3777-3783 (1995), or Rump et al., *Bioconj. Chem.* 9:341-349 (1995). Typically, conjugation is achieved through the use of a suitable functional groups at an oligonucleoside terminus. For example, the 3'-amino group present at the 3'-terminus of NP- and NPS-linked oligonucleosides can be reacted with carboxylic acids, acid chlorides, anhydrides and active esters, using suitable coupling catalysts, to form an amide linkage. Thiol groups are also suitable as functional groups (see Kupihar et al., *Bioorg. Med. Chem.* 9:1241-1247 (2001)). Various amino- and thiol-functionalized modifiers of different chain lengths are commercially available.

Specific approaches for attaching lipid groups to a terminus of an NP- or NPS-linked oligonucleoside include those described in US Appn. Pubn. No. 2005/0113325, which is incorporated herein by reference. In addition to the amide linkages noted above, for example, lipids may also be attached to the oligonucleoside chain using a phosphoramidite derivative of the lipid, to produce a phosphoramidate or thiophosphoramidate linkage connecting the lipid and the oligonucleoside. The free 3'-amino group of the fully protected support-bound oligonucleoside may also be reacted with a suitable lipid aldehyde, followed by reduction with sodium cyanoborohydride, which produces an amine linkage.

For attachment of a lipid to the 5' terminus, as also described in US Appn. Pubn. No. 2005/0113325, the oligonucleoside can be synthesized using a modified, lipid-containing solid support. Reaction of 3-amino-1,2-propanediol with a fatty acyl chloride (RC(O)Cl), followed by dimethoxytritylation of the primary alcohol and succinylation of the secondary alcohol, provides an intermediate which is then coupled, via the free succinyl carboxyl group, to the solid support. An example of a modified support is shown below, where S— represents a long chain alkyl amine CPG support, and R represents a lipid.

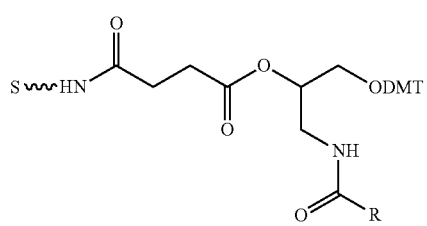

This procedure is followed by synthesis of the oligonucleoside in the 5' to 3' direction, as described, for example, in Pongracz & Gryaznov (1999), starting with deprotection and phosphitylation of the —ODMT group. This is effective to produce, for example, the following structure, after cleavage from the solid support:

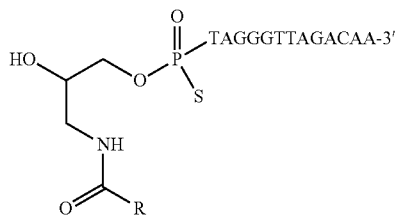

The structure above, when —R is —$(CH_2)_{14}$—$CH_3$ (such that —C(O)R is palmitoyl) and all internucleoside linkages are NPS linkages, is designated herein as GRN163L.

All oligonucleosides, except the shorter versions of GRN163L, were synthesized using methods previously described (Gryaznov et al., 2001; Herbert et al., 2005; Herbert et al., 2002). The compounds were analyzed and purified by reverse phase (RP) and ion exchange (IE) HPLC and characterized by $^{31}$P NMR, mass spectrometry, and PAGE. Truncated versions of GRN163L ((11-mer, 9-mer, and 7-mer) were purchased from Transgenomic Inc. (Omaha, Nebr.). The prepared oligonucleosides were solubilized in normal saline and their concentrations were determined by UV spectroscopy. The compounds were then evaluated as anti-adhesion agents and/or telomerase inhibitors.

Telomerase Activity Assay

Telomerase activity from cell extracts was analyzed using a PCR-based telomeric repeat amplification protocol assay (TRAP assay), as described in Herbert et al., 2002. Samples were resolved on a 10% polyacrylamide gel and scanned using a STORM 860 PhosphorImager scanner system (MolecularDynamics). Quantitation and visualization of the TRAP gels was done as described in Chai et al., 2002.

Generation of Lentiviral shhTR-A549luc Cells and Adenoviral hTERT-A549luc Cells

The pHRIU1hTR-CMVGFPWSin18 vector that delivers a shRNA (short hairpin RNA) directed towards the hTR was a gift from Dr. Elizabeth Blackburn (University of California at San Francisco, San Francisco, Calif.). Five μg of pMD.G plasmid, 10 μg of pCMVDR8.91, and 15 μg of lentivector were cotransfected into 293T cells using calcium phosphate precipitation. Conditioned medium was harvested at 48 h after transfection and filtered through 0.45-μm filters. For lentivirus infection, A549luc cells (70% confluent) were incubated with culture medium-diluted viral supernatant (20-40 transduction units/cell) supplemented with polybrene (8 μg/ml) for 16 h.

A549luc cells (70% confluent) were exposed to Adenoviral hTERT (AdhTERT) (30 MOI) for 16 h in medium without serum. The virus was then removed and complete medium was then added. Transfection frequency was ≥75% after 24 h.

Immunofluorescence

A549luc and A549luc-AdhTERT cells ($1 \times 10^4$/300 μl media) were seeded into 8-well chamber slides and allowed to attach overnight. Then the cells were fixed in 4% PAF and permeabilized with 0.1% TritonX-100. Non-specific sites were blocked with 0.5% BSA in PBS. The slides were incubated with anti-mouse hTERT antibody (5 μg/ml) kindly provided by Geron Corporation (Menlo Park, Calif.). The slides were then incubated with Rhodamine-conjugated goat-anti-mouse IgG (Jackson ImmunoResearch Laboratory, Inc., West Grove, Pa.). The slides were washed twice for 15 min each with PBS, mounted with Vectoshield+Dapi (Vector Laboratories, Inc., Burlingame, Calif.), and viewed using a Zeiss Axiovert 200M microscope using an AXIO Cam MRM REV2 camera attached with a C-Mount 0.63× adaptor and an X-CITE 120 IRIS fluorescent light source. All original pictures were taken using a magnification of 20×.

hTR RT-PCR

Total cellular RNA was extracted from cultured cells using RNeasy Mini Kit (Qiagen) according to manufacturer's instructions. RT-PCR was performed using one-step RT-PCR kit (Invitrogen) using the following primers for hTR: F3B-hTR: 5' TCT AAC CCT AAC TGA GAA GGG CGT AG-3'; Htr189R: 5' CCA GCA GCT GAC ATT TTT TG-3' as previously reported (Yi et al., 1999). As internal controls for the quantity and quality of the RNA specimens, RT-PCR amplifications targeting transcripts of the housekeeping gene glyceraldehyde-3-phosphate dehydrogenase (GAPDH) were performed in parallel.

Cell Attachment and Spreading Assays

Cell attachment and spreading were carried out following the methodology, described in Current Protocols in Cell Biology (Cell-Substrate Adhesion Assays 9.1). Briefly, individual wells in a 96-well plate (NalNunc) were coated overnight at 4° C. with Type I collagen (1-25 μg/ml in Dulbecco's PBS) (BD Biosciences). The un-attached collagen was aspirated and the wells were blocked with heat-denatured BSA (10 mg/ml) overnight at 4° C. The BSA solution was aspirated and the wells were washed with DPBS. A549luc cells were trypsinized briefly and detached quickly. Cells ($1 \times 10^5$/ml for spreading and $1 \times 10^6$/ml for attachment) were resuspended gently in conditioned medium (DMEM-Hepes-10% FBS gassed with 5% (v/v) $CO^2$ for 20-30 min). Care was taken to guard against cell clumping and aggregation. Cells in conditioned media were placed in a 37° C. incubator with the lid off for 10-15 min to allow for the recovery from trypsinization, and the re-expression of cell surface molecules that mediate cell attachment and spreading. Test compounds and/or MM or GRN163L oligonucleotides were diluted with DPBS, and 50 μl of the diluted compounds were added to the wells, then 50 μl of conditioned cells were added to the wells.

For attachment assays, conditioned cells were incubated with test or control compound (1 μM) for 20 min at 37° C. with the lid off. Wells were washed 3 times with DPBS, and cells were fixed with 5% glutaraldehyde (Sigma) for 20 min at RT. The fixed cells were washed 3 times with $dH_2O$, and cells were stained with filtered 0.1% crystal violet diluted in 200 mM 2-(N-morpholino)ethanesulfonic acid (MES), pH 6 for 1 h at RT. Wells were washed 3 times with 400 μl $dH_2O$, and the dye was solubilized in 10% acetic acid for 15 min on an orbital shaker. Absorbance was measured at 570 nm using a microtiter plate reader. Data are expressed as relative attachment which is equivalent to absorbance.

For spreading assays, conditioned cells were incubated with test or control compound (1 μM) for 90 min at 37° C. with the lid off Media were aspirated and cells were fixed directly with 5% glutaraldehyde for 30 min at RT. Fixative was aspirated and cells were stored at 4° C. in calcium and magnesium free DPBS plus sodium azide. Cells were view on an inverted phase-contrast microscope at 20× magnification using a Zeiss Axiovert 200M microscope equipped with an AXIO Cam MRM REV2 camera attached with a C-Mount 0.63× adaptor. Total cell surface area was quantified with Axio Vision (version AxioVs40 V 4.4.1.0).

Xenograft Mice Experiments and Bioluminescence In Vivo Imaging of A549luc Cells

Immunodeficient mice (nu/nu; Harlan Sprague-Dawley, Inc., Indianapolis, Ind.) were maintained in pathogen free conditions within the animal resources center (ARC) at the University of Texas Southwestern Medical Center and treated according to ARC and IACUC guidelines. Mice were irradiated with 3.5 Gy $^{137}$Cs 18 to 24 h before tail vein injections with A549luc cells. The cell viability was checked via trypan blue exclusion and $1\times10^6$ cells/100 µl sterile PBS were injected into the tail vein of 4 mice per group. Immediately after cell inoculation, mice were given a single dose of either MM (15 mg/kg) or GRN163L intraperitoneally (i.p.).

Mice were imaged weekly using a novel light emission tomography system (LETS) as previously described (Dikmen et al., 2005). Briefly, light sensitive D-luciferin substrate (Biosynth, Naperville, Ill.) was injected (450 mg/kg) i.p. just prior to isofluran (1.5%) anesthesia. All images were taken for 10 minutes. Signal intensity was quantified as the sum of all detected photon counts within the region of interest after subtraction of background luminescence using Igor Pro software.

Example 1. Rapid Morphological Alterations Induced by GRN163L

Figure 1B:
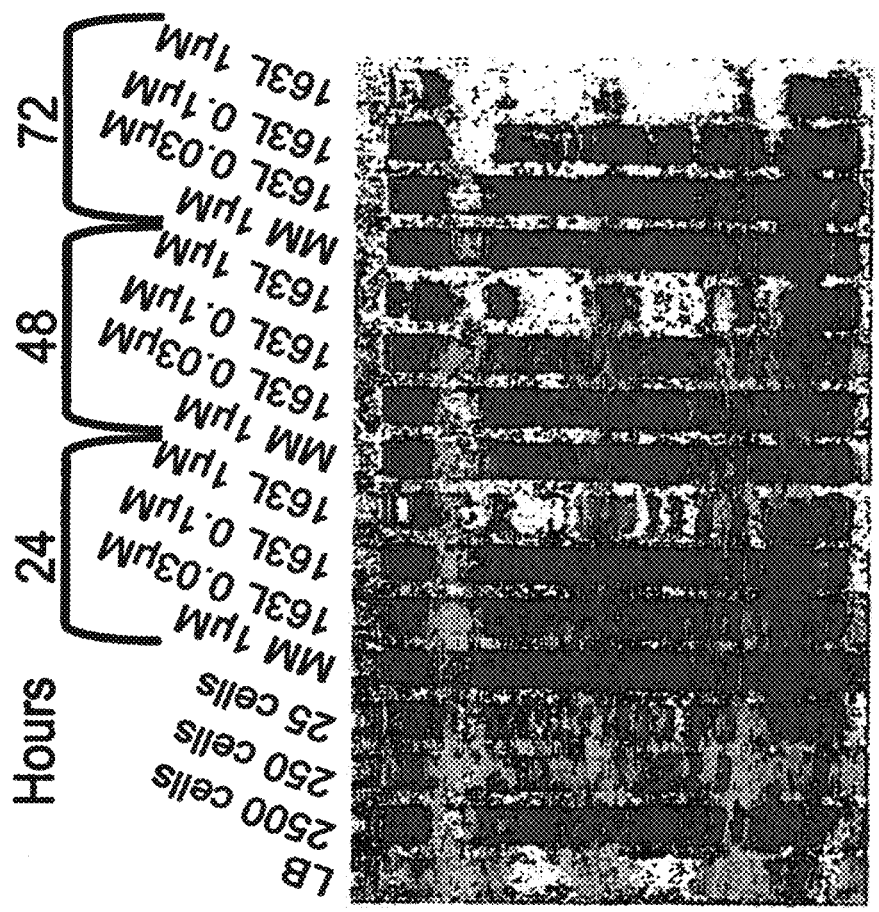
Figure 1C:
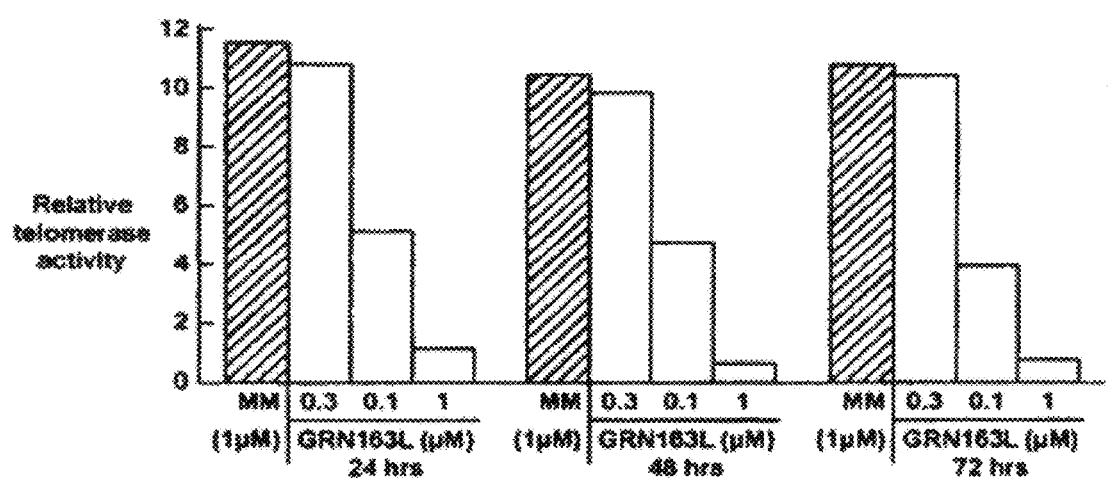
FIG. 1C: Quantification of TRAP activity gel from FIG. 1B.

A549-luc cells were treated prior to cell attachment with a single 1 µM dose of either GRN163L (163L) or mismatch control oligonucleotide (MM), and cell morphology was assessed after 24, 48 and 72 hours of incubation, by means of phase contrast photomicrographs (FIG. 1A).

After 24 hours, the control-treated cells exhibited a typical epitheloid appearance, with properly attached flattened cytoplasmic extensions and evidence of proliferation, while the GRN163L-treated cells were weakly attached and rounded, some having thin elongated cytoplasmic extrusions. This altered cellular phenotype was persistent after 48 and 72 hours of treatment (FIG. 1A).

Inhibition of telomerase activity (approx. 94% reduction) was also observed for up to 72 hours in the GRN163L-treated cells, while telomerase activity in the control cells was unaffected (FIGS. 1B and 1C: Lane 1, negative control (lysis buffer); Lanes 2-4, positive controls (H1299 cells (2500, 250 and 25 cells)); Lanes 5-8, 24 hr treatment of MM or GRN163L, Lanes 9-12, 48 hr treatment of MM or GRN163L and Lanes 13-16, 72 hr treatment of MM or GRN163L).

Similar results were obtained in at least 5 independent experiments.

Example 2. Altered Cell Morphology Induced by Oligonucleotide Agents Such as GRN163L is Independent of Human Telomerase RNA (hTR) and Telomerase Holoenzyme Activity To determine if the altered cellular phenotype induced by GRN163L, as described in Example 1, was tied to telomerase activity or its inhibition, the effect of GRN163L on SUSM-1 immortalized liver fibroblasts and VA13 lung fibrosarcoma cells, neither of which expresses endogenous hTR, was examined.

A549-luc, A549-luc shhTR, VA13 (hTR negative) and normal BJ cells were treated prior to cell attachment with either 1 µM of MM (mismatch control oligonucleotide) or GRN163L, and phase contrast photomicrographs (20×) were taken after 24 hours of treatment (FIG. 2A). Similar results were obtained in at least 3 independent experiments. Both of the hTR-negative cell lines were altered morphologically by GRN163L (FIG. 2A), while normal BJ foreskin fibroblasts, which do express low-to-moderate levels of hTR (data not shown), were not affected by GRN163L. This result provides evidence that hTR per se is not involved in the altered morphology induced by GRN163L.

RT-PCR analysis of hTR levels in VA13, VA13hTR, A549 and A549shhTR cells is shown in FIG. 2B. FIG. 2B shows the RT-PCR confirmation of the lack of hTR expression in SUSM-1 and VA13 cells; VA13 cells that overexpress hTR (VA13hTR) were used as a positive control.

A549-luc cells were treated prior to cell attachment with either 1 µM of 13-mer MM, 13-mer GRN163L or truncated (7-mer) 163L, and phase contrast photomicrographs (20×) were taken after 24 hours of treatment (FIG. 2C). Similar results were obtained in 3 independent experiments.

Twenty-four hour TRAP analysis of A549-luc cells treated prior to cell attachment with 1 or 10 µM of either 13-mer MM or truncated oligomers of GRN163L, respectively, is shown in FIG. 2D: Lane 1, negative control (lysis buffer); Lanes 2-4, positive controls (H1299 cells (2500, 250 and 25 cells)); Lane 5, no treatment; Lanes 6-7, 13-mer MM; Lanes 8-9, 13-mer GRN163L; Lanes 10-11, 11-mer truncated GRN163L; Lanes 12-13, 9-mer truncated GRN163L; Lanes 14-15, 7-mer truncated GRN163L. Similar results were obtained in a separate independent experiment.

The truncated versions of GRN163L, which exert low-to-moderate inhibition of telomerase, were tested to determine the role of telomerase inhibition and/or oligonucleotide length in the alteration of A549 cell adhesion (Table 1). A459-luc cells were treated with a single 1 µM dose of either MM (control), 13-, 11-, 9- or 7-mer GRN163L-derived oligonucleotides at the time of cell attachment. The treatment was carried out for 24 hours, and telomerase activity was measured, following analysis of cell morphology.

All three of the shorter oligomers (11-mer, 9-mer and 7-mer) caused the altered cell phenotype within 24 hours (FIG. 2C) (11-mer and 9-mer data not shown) to the same extent as the full-length 13-mer. As expected, the truncated oligomers (11-mer, 9-mer and 7-mer) had varying abilities to inhibit telomerase activity when compared with the full-length 13-mer GRN163L (FIG. 2D). For example, at this concentration (1 µM) the 7-mer oligonucleotide only minimally inhibited telomerase activity (FIG. 2D), yet it induced the anti-adhesive effect (FIG. 2C).

Example 3. Altered Cell Morphology is Independent of Telomere Length

Figure 3A:
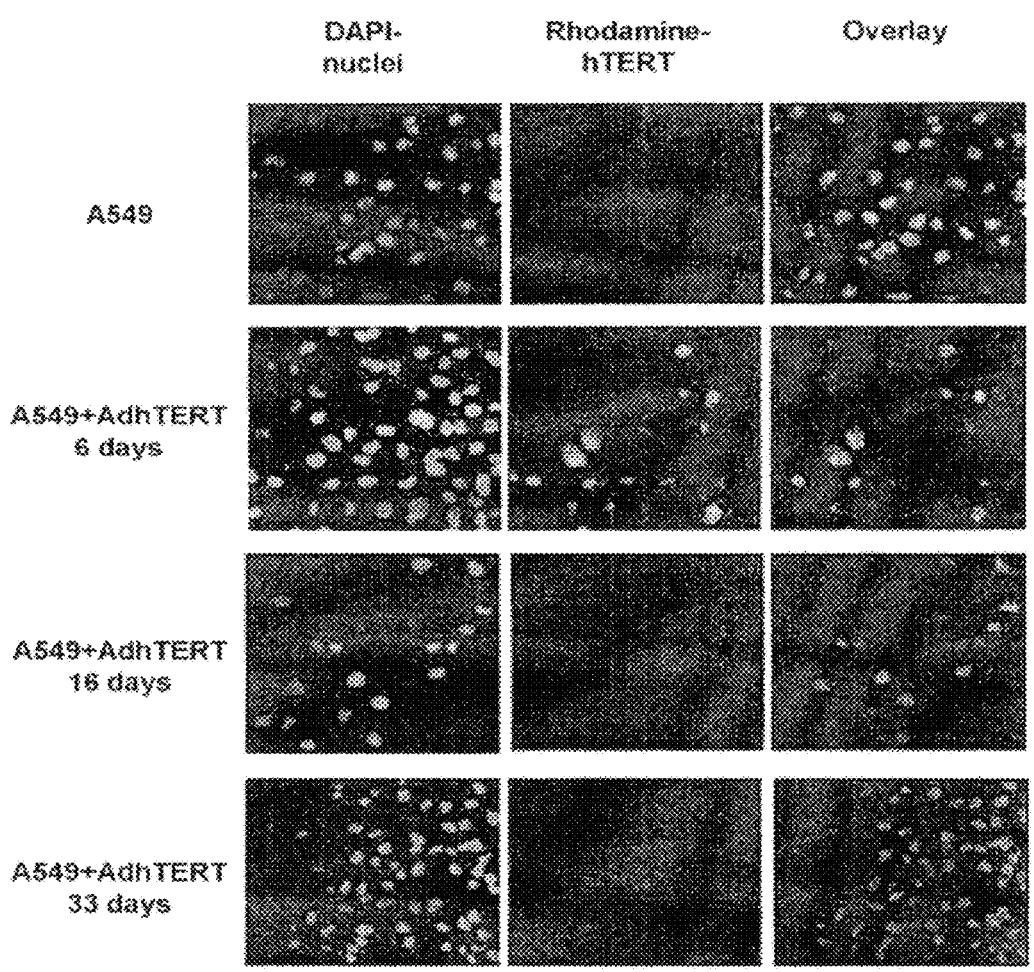
FIGS. 3A-D show telomere length-independence of GRN163L-induced altered A549-luc cell morphology.

Telomeres in A549-luc cells were transiently elongated via the introduction of adenoviral hTERT, which allows for ectopic expression of the catalytic component of telomerase. The elongated telomere phenotype was allowed to propagate through 20-30 population doublings, utilizing a monoclonal antibody (GRN 1A4) that is capable of discriminating between endogenous and exogenous hTERT to detect the exogenously overexpressed AdhTERT (FIG. 3A). The transient infection with AdhTERT also produced a 3-fold increase in TRAP activity after 6 days of infection.

Control A549-luc cells treated with a single 1 µM dose of GRN163L at the time of seeding exhibited an altered cell morphology after 24 hours of incubation (FIG. 3D, top row), as did the A549-luc cells with adenovirally elongated telomeres, which clearly remain susceptible to the rapid morphological changes induced by GRN163L (second and third rows). These experiments suggest that critically short telomere length on some chromosomes is not required for the morphological changes induced by GRN163L.

Immunofluorescent localization of rhodamine-labeled adenoviral hTERT in A549-luc cells after 6, 16 and 33 days of infection is shown in FIG. 3A.

Figure 3B:
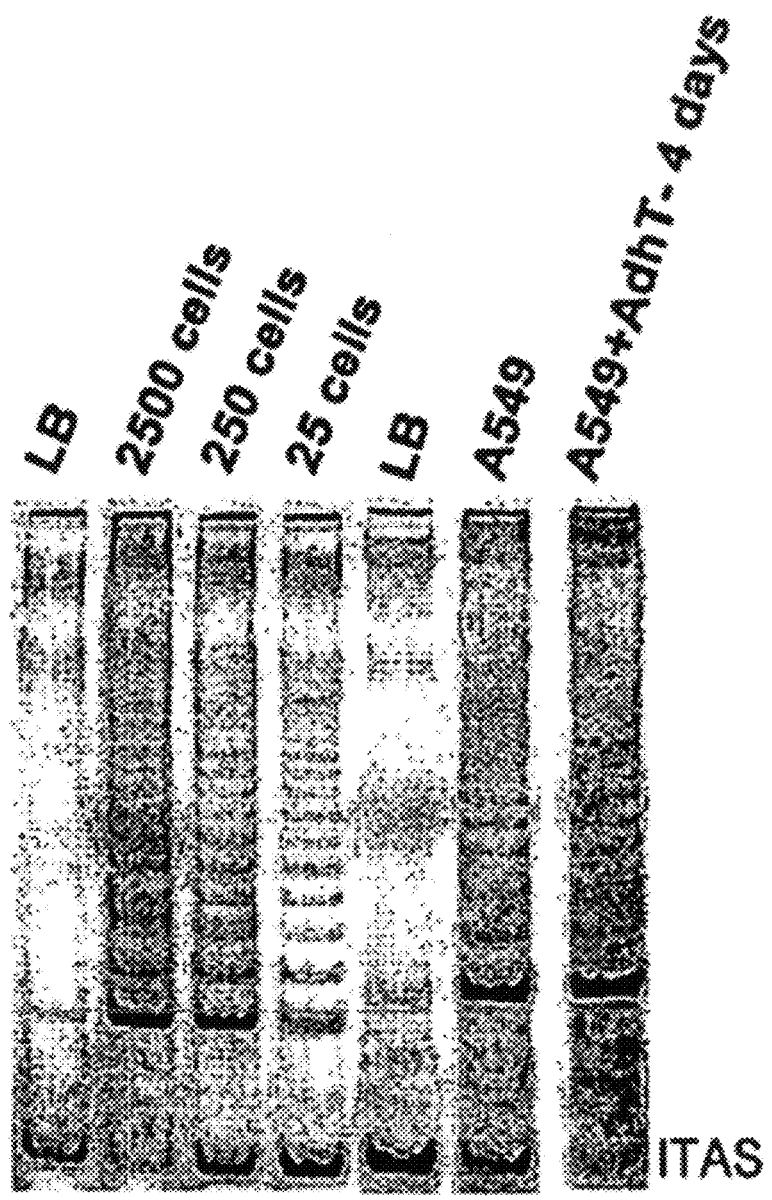
Figure 3C:
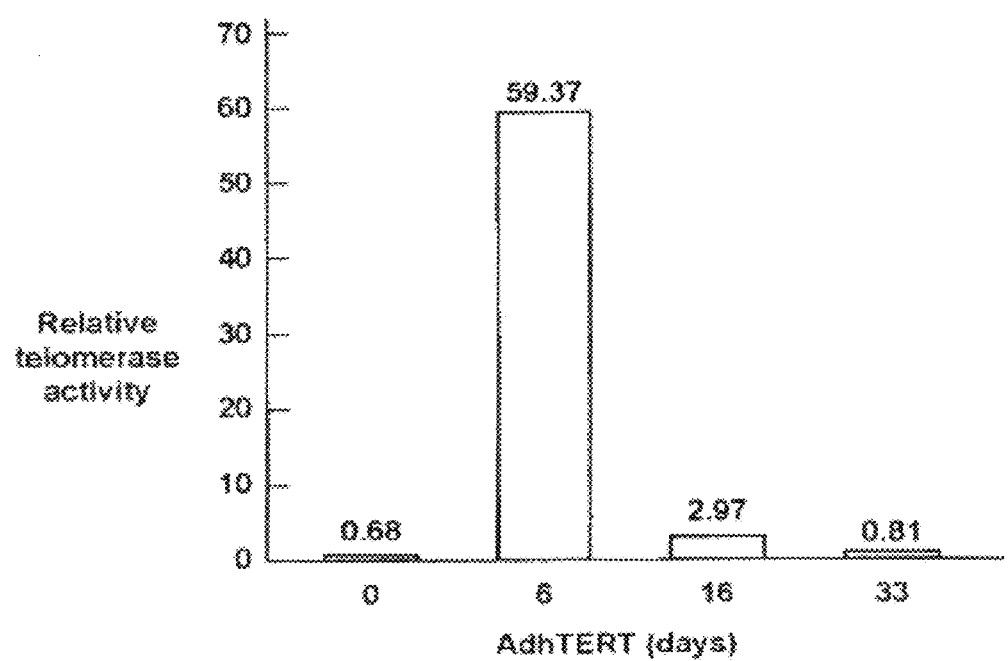

TRAP analysis of A549-luc cells infected transiently with adenoviral hTERT is shown in FIG. 3B: Lane 1, negative control (lysis buffer); Lanes 2-4, positive controls (H1299 cells (2500, 250 and 25 cells)); Lane 5, negative control (lysis buffer); Lane 6, A549-luc; Lane 7, A549-luc+adenohTERT 4 days. (Data for A549-luc+adenohTERT 16 days and A549-luc+adenohTERT 33 days not shown.) Quantification of the TRAP activity gel, including data for A549-luc+adenohTERT 16 days and A549-luc+adenohTERT 33 days, is shown in FIG. 3C.

Figure 3D:
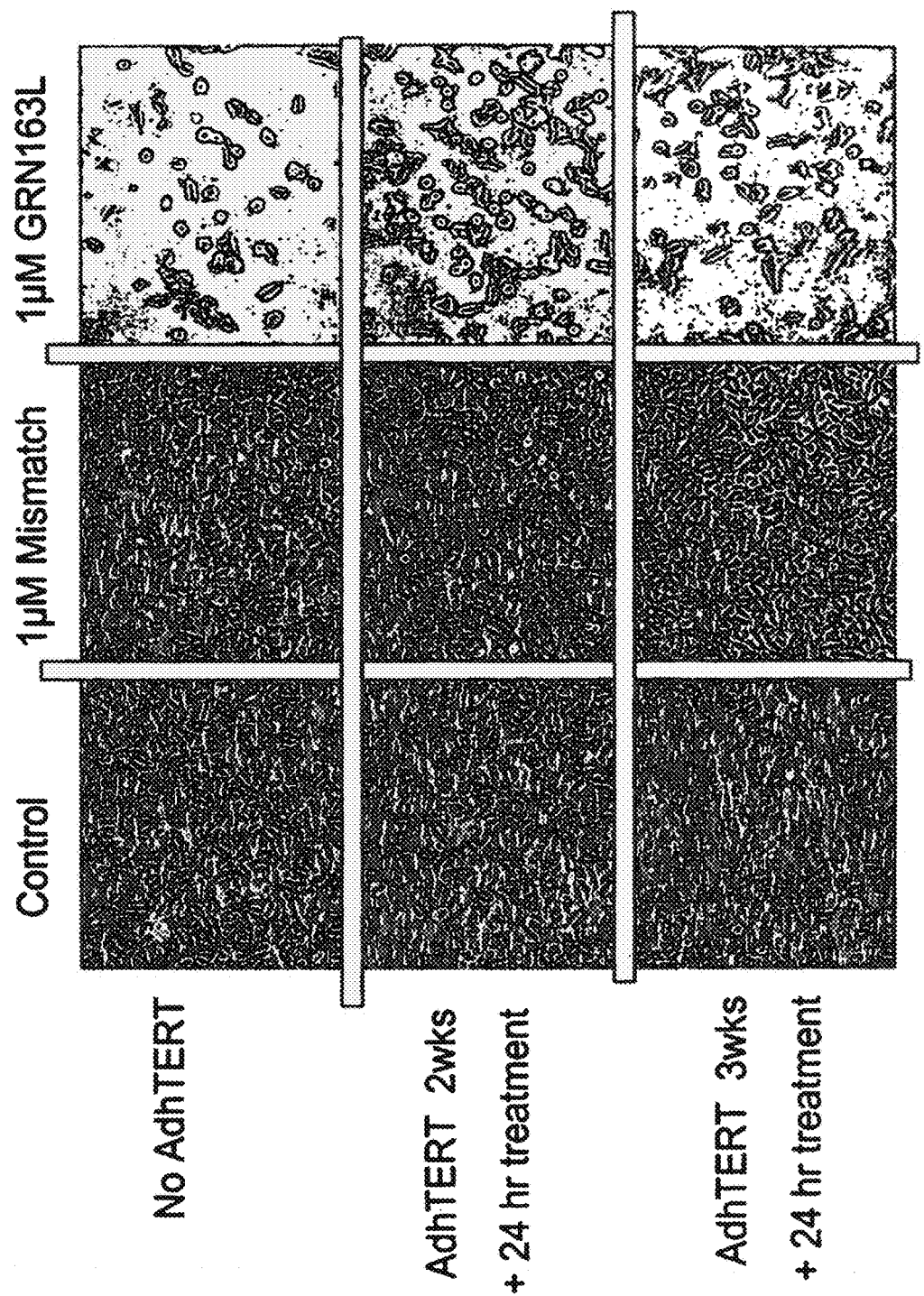

A549-luc and A549-luc+AdhTERT 2 and 3 weeks post-infection were treated prior to cell attachment with either 1 µM of MM or 163L, and phase contrast photomicrographs (20×) were taken after 24 hours of treatment, as shown in FIG. 3D. Similar results were obtained in a separate independent experiment.

Example 4. GRN163L-Induced Altered A549-Luc Cell Adhesion is Due to a Reduction in Cell Attachment and an Inhibition of Cell Spreading To determine if the rapid morphological alterations were related to a dysfunction in cell adhesion, A549-luc cells were treated prior to cell attachment (top row) or after overnight attachment (bottom row) with a single dose of either 1 µM MM-Control or GRN163L (FIG. 4A). Interestingly, GRN163L only alters cell adhesion when the cells are treated at the time or prior to cell attachment (e.g. within 4 hours of plating). FIG. 4A also shows that cells allowed to attach to the substrata overnight, are not morphologically altered when further tested by treatment with GRN163L. The cells treated post-attachment with GRN163L resemble the MM-treated cells also treated post-attachment. Similar results were obtained in at least 5 independent experiments. These findings suggest that a yet unknown aspect of cell adhesion is involved in this anti-adhesive phenomenon induced by GRN163L.

Utilizing a colorimetric assay to determine cell attachment efficiency, FIG. 4B (left graph) shows that A549-luc cells treated prior to cell attachment with a single dose of 1 µM GRN163L (163L) for 20 minutes exhibit a 50% reduction in the ability to attach to plastic substrata, when compared to cells treated concomitantly with 1 µM MM-Control. Interestingly, cells that were treated while in suspension with a single dose of GRN163L, but were seeded into wells coated with Type I collagen (1-25 µg/ml), did not exhibit any differences in attachment efficiency when compared to MM-Control treated cells. Thus, type I collagen blocks the GRN163L-induced reduction in cell attachment. Importantly, A549-luc cells that were allowed to attach to the plastic substrata for 1-4 hours, were resistant to the anti-adhesive effect of GRN163L; since there were no differences between the post attachment efficiency of MM versus GRN163L-treated cells (FIG. 4B-right graph). Similar results were obtained in at least 3 independent experiments.

The alteration in cell adhesion in the GRN163L-treated cells may also be attributed to an inhibition of cell spreading, which is the physiological extension of cell attachment. FIG. 4C (left panel) shows that A549-luc cells treated prior to cell attachment with a single dose of 1 µM GRN163L for 90 minutes have incomplete cytoplasmic protrusions coupled with retarded cell flattening, whereas cells treated with 1 µM MM-Control appear well spread with numerous lamelipodia (FIG. 4C-left panel). Quantitatively, the GRN163L-treated cells had a 57% reduction in total cell surface area (FIG. 4D) when compared to MM-treated cells. Similar results were obtained in at least 3 independent experiments.

Consistent with the data shown in the morphological analysis (FIG. 4A), and the attachment assays (FIG. 4B), cells that were treated while in suspension with a single dose of GRN163L, but were seeded into wells coated with Type I collagen (25 µg/ml), did not exhibit any differences in the ability to spread and flatten out when compared to MM-Control treated cells (FIGS. 4C and D). Thus, type I collagen blocks the GRN163L-induced inhibition of cell spreading. Importantly, A549-luc cells that were allowed to attach to the plastic substrata for 1 hour, were slightly less resistant to the anti-cell adhesive effect of GRN163L; since there was only a 22% reduction in cell spreading between the MM and GRN163L-treated cells (FIGS. 4C and D-right panels).

Example 5. A Single Dose of GRN163L Administered In Vivo Reduces A549-Luciferase Cell Metastasis to the Lung A human xenograft model of lung cancer metastasis was employed to determine the effect of a single intraperitoneal dose of GRN163L (15 mg/kg) administered at the time of intravenous A549-luc lung cancer cell inoculation in athymic nude mice.

Figure 5A:
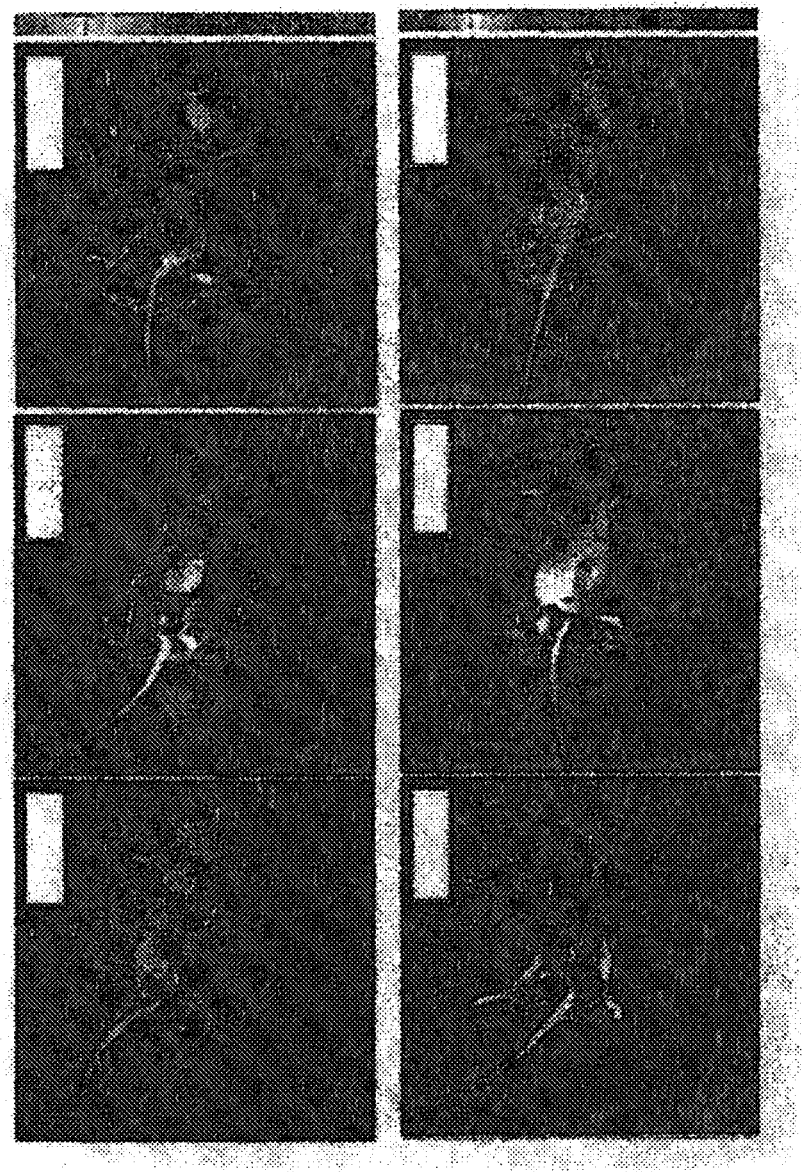
FIGS. 5A-B show the anti-metastatic effect of GRN163L on A549-luciferase (A549-Luc cells, 1×$10^6$) in vivo.
Figure 5B:
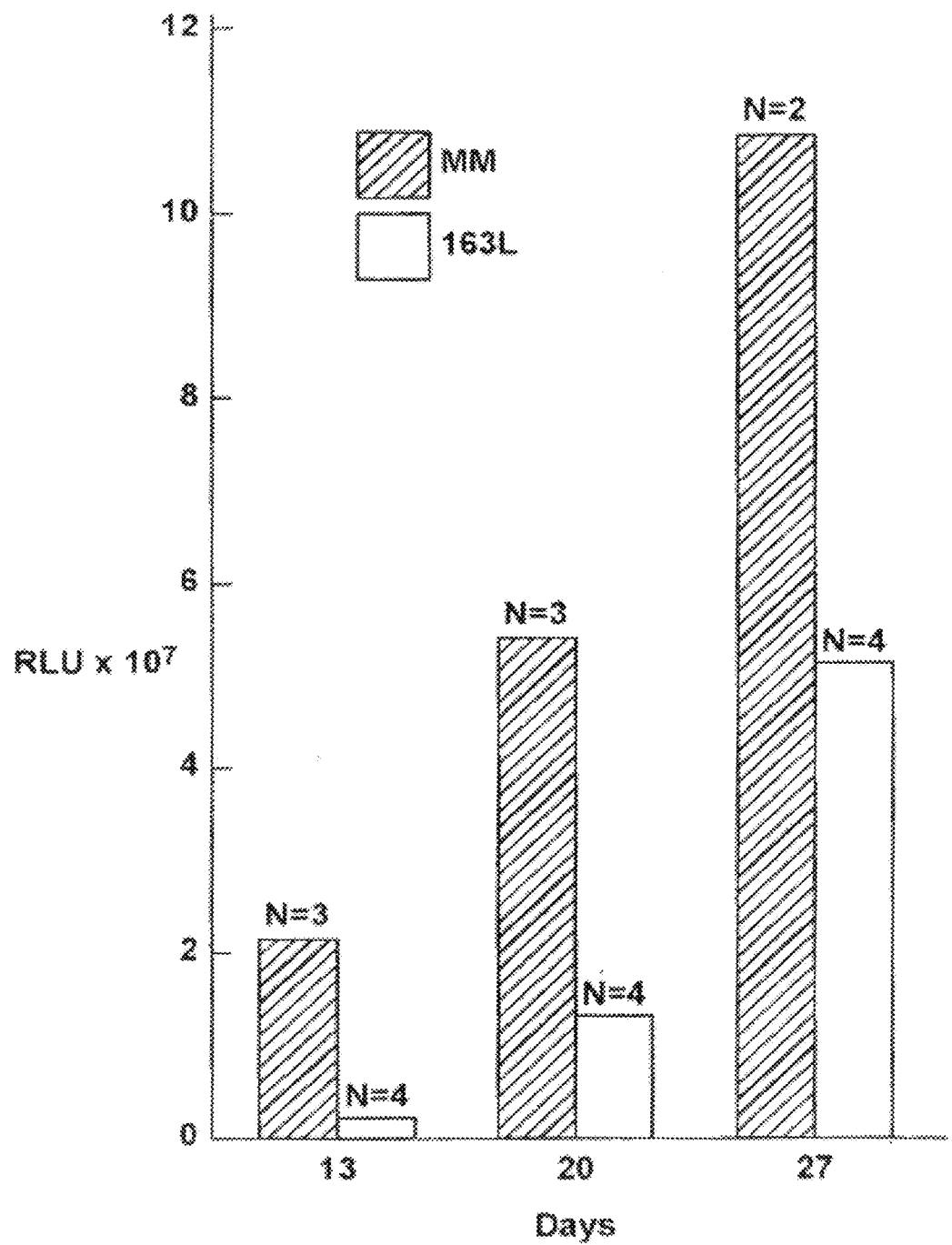

A549-Luc cells were injected via the tail vein into immunodeficient mice. The animals were administered a single dose of either MM (15 mg/kg) or GRN163L (15 mg/kg) intraperitoneally at the time of cell inoculation. Bioluminescent images (BLI) of the Lucifer's-expressing A549 cells were recorded at days 13, 20 and 27 of tumor progression (FIG. 5A). Average BLI signals are depicted graphically in FIG. 5B. Similar results were obtained in three independent experiments.

A single dose of GRN163L (15 mg/kg) resulted in a 92%, 76% and 53% reduction in tumor load at days 13, 20 and 27 of tumor progression, respectively, as determined by bioluminescent imaging of the luciferase-expressing A549 cells, when compared with the MM-treated (15 mg/kg) controls.

Since reductions in A549-luc cell attachment and spreading were found in vitro (FIG. 4), one interpretation of these finding is that the anti-adhesive effects of GRN163L may be related at least in part to the reductions in lung tumor burden found in vivo in this experimental model of metastasis.

SEQUENCE TABLE

SEQ ID NO: 1 (5' to 3'):
```
GGGUUGCGGA GGGUGGGCCU GGGAGGGGUG GUGGCCAUUU      60
UUUGUCUAAC CCUAACUGAG

AAGGGCGUAG GCGCCGUGCU UUUGCUCCCC GCGCGCUGUU     120
UUUCUCGCUG ACUUUCAGCG

GGCGGAAAAG CCUCGGCCUG CCGCCUUCCA CCGUUCAUUC     180
UAGAGCAAAC AAAAAAUGUC

AGCUGCUGGC CCGUUCGCCC CUCCCGGGGA CCUGCGGCGG     240
GUCGCCUGCC CAGCCCCGA

ACCCCGCCUG GAGGCCGCGG UCGGCCCGGG GCUUCUCCGG     300
AGGCACCCAC UGCCACCGCG

AAGAGUUGGG CUCUGUCAGC CGCGGGUCUC UCGGGGCGA      360
GGGCGAGGUU CAGGCCUUUC
```

| SEQUENCE TABLE-continued | |
|---|---|
| AGGCCGCAGG AAGAGGAACG GAGCGAGUCC CCGCGCGCGG CGCGAUUCCC UGAGCUGUGG | 420 |
| GACGUGCACC CAGGACUCGG CUCACACAUG C | 451 |

| SEQ ID NO: | Sequence (5' to 3') |
|---|---|
| 2 | TAG GGT TAG ACA A |
| 3 | TAG GTG TAA GCA A |

| SEQUENCE TABLE-continued | |
|---|---|
| 4 | CGT ACC ACG CTC GCT A |
| 5 | CTA GAC TCG GAC CCT C |
| 6 | AAC GTT GAG GGG CAT |
| 7 | AAC GAG TTG GGG CAT |
| 8 | GTG AAG GCG GCA GG |

It is claimed:

1. A method of inhibiting cell adhesion, comprising contacting said cells with a compound having a structure represented by o-(x-L)n, where (a) o is a polynucleoside moiety comprising a sequence of nucleosides and linkage moieties, wherein (i) at least 50% of said linkage moieties are selected from: 3'-NH—P(O)(S$^-$)-5'; 3'-NH—P(O)(S—)—{OR}$_m$—Y—P(O)(S$^-$)-5'; and 3'-Y—R—O—P(O)(S$^-$)-5', where Y is NH or O; R is a stable linear chain two to six atoms in length having bonds selected from alkyl, alkenyl, ether, thioether, and amino; and m is 1 to 3; and (ii) said sequence includes at least one motif selected from GGG and GG(W)$_{1-3}$GG, containing residues G and/or W, where G is guanosine and W is a nucleoside or the moiety —O—R—, where R is as defined above, and the inter-residue linkages within said motif are N3'→P5' thiophosphoramidate (3'-NH—P(O)(S—)-5') or phosphorothioate (3'-O—P(O)(S—)-5') linkages; (b) x is an optional linker group, (c) L is a lipid moiety, and (d) n is 1 or 2; wherein the compound is not a telomerase inhibitor.

2. The method of claim 1, wherein said cells are cancer cells.

3. The method of claim 1, wherein Y is NH.

4. The method of claim 1, wherein m is 1.

5. The method of claim 1, wherein said inter-residue linkages are 3'-NH—P(O)(S$^-$)-5' (NPS) linkages.

6. The method of claim 1, wherein at least 50% of internucleoside linkages are 3'-NH—P(O)(S$^-$)-5' (NPS) linkages.

7. The method of claim 1, if wherein R is a stable linear chain three to five atoms in length having bonds selected from alkyl and ether linkages.

8. The method of claim 1, wherein R is —(CH$_2$)$_n$—, where n is 3 to 5.

9. The method of claim 1, wherein the sum of nucleosides and groups —OR— in the polynucleoside moiety o is from 5 to about 30.

10. The method of claim 1, wherein the sum of nucleosides and groups —OR— in the polynucleoside moiety o is from 7 to about 15.

11. The method of claim 1, wherein o contains a sequence motif of at least three consecutive guanosine (G) nucleosides directly linked by NPS linkages.

12. The method of claim 1, wherein o contains a sequence motif GG(W)$_{1-3}$GG, where G is guanosine and W is a nucleoside, and the linkages within said motif are N3'→P5' thiophosphoramidate (NPS) linkages.

13. The method of claim 1, wherein the lipid L is selected from a linear hydrocarbon, a fatty acid, and a fatty acid derivative, and is attached to the 3' or 5' terminus of said oligonucleoside.

14. The method of claim 13, wherein the lipid L is a C12 to C24 linear hydrocarbon.

15. The method of claim 14, wherein the lipid L is a palmitic or oleic acid derivative and is attached to said terminus via a glycerol or aminoglycerol linker.

* * * * *